(12) United States Patent
Armani et al.

(10) Patent No.: US 9,409,870 B2
(45) Date of Patent: Aug. 9, 2016

(54) COMPOUNDS

(71) Applicant: CHIESI FARMACEUTICI S.p.A., Parma (IT)

(72) Inventors: Elisabetta Armani, Parma (IT); Carmelida Capaldi, Parma (IT); Jonathan Mark Sutton, Harlow (GB); Robert Andrew Heald, Harlow (GB)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 14/953,183

(22) Filed: Nov. 27, 2015

(65) Prior Publication Data
US 2016/0168101 A1    Jun. 16, 2016

(30) Foreign Application Priority Data
Dec. 15, 2014   (EP) .................................... 14198044

(51) Int. Cl.
| | | |
|---|---|---|
| *A61K 31/513* | (2006.01) | |
| *C07D 233/70* | (2006.01) | |
| *C07D 403/04* | (2006.01) | |
| *C07D 405/14* | (2006.01) | |
| *C07D 403/14* | (2006.01) | |
| *C07C 309/29* | (2006.01) | |
| *C07C 53/06* | (2006.01) | |
| *C07D 401/14* | (2006.01) | |

(52) U.S. Cl.
CPC .............. *C07D 233/70* (2013.01); *C07C 53/06* (2013.01); *C07C 309/29* (2013.01); *C07D 401/14* (2013.01); *C07D 403/04* (2013.01); *C07D 403/14* (2013.01); *C07D 405/14* (2013.01)

(58) Field of Classification Search
USPC .................................. 514/183, 248, 359, 381
See application file for complete search history.

(56) References Cited

U.S. PATENT DOCUMENTS

| | | | |
|---|---|---|---|
| 2006/0100204 A1 | 5/2006 | Cogan et al. | |
| 2014/0018345 A1 | 1/2014 | Capaldi et al. | |

FOREIGN PATENT DOCUMENTS

| | | |
|---|---|---|
| EP | 2 740 728 | 6/2014 |
| WO | 2007/129962 | 11/2007 |

OTHER PUBLICATIONS

Hall; Acta Crystallographica Section E: Structure Reports Online (2013), 69(7), o1102-o1103.*
Extended European Search Report in Application No. 14198044.1 issued Mar. 18, 2015.

* cited by examiner

*Primary Examiner* — Pancham Bakshi
(74) *Attorney, Agent, or Firm* — Oblon, McClelland, Maier & Neustadt, L.L.P.

(57) ABSTRACT

Compounds of formula (I) described herein are imidazolone derivatives having human neutrophil elastase (HNE) inhibitory properties and are useful for the treatment of diseases and conditions in which HNE is implicated.

12 Claims, No Drawings

COMPOUNDS

CROSS REFERENCES TO RELATED APPLICATIONS

This application claims priority to European Patent Application No. 14198044.1, filed on Dec. 15, 2014, which is incorporated herein by reference in its entirety.

BACKGROUND OF THE INVENTION

1. Field of the Invention

The present invention relates to heterocyclic compounds, which are imidazolone derivatives having human neutrophil elastase inhibitory properties, and their use in therapy.

2. Discussion of the Background

Human neutrophil elastase (HNE) is a 32 kDa serine proteinase found in the azurophilic granules of neutrophils. It has a role in the degradation of a wide range of extracellular matrix proteins, including fibronectin, laminin, proteoglycans, Type III and Type IV collagens as well as elastin (see Bieth, G. In Regulation of Matrix accumulation, Mecham, R. P. (Eds), Academic Press, NY, USA 1986, 217-306, which is incorporated herein by reference in its entirety). HNE has been for long considered to play an important role in homeostasis through repair and disposal of damaged tissues via degradation of the tissue structural proteins. It is also relevant in the defense against bacterial invasion by means of degradation of the bacterial body. In addition to its effects on matrix tissues, HNE has been implicated in the upregulation of IL-8 gene expression and also induces IL-8 release from the epithelial cells of the lung. In animal models of Chronic Obstructive Pulmonary Disease (COPD) induced by tobacco smoke exposure both small molecule inhibitors and protein inhibitors of HNE inhibit the inflammatory response and the development of emphysema (see Wright, J. L. et al. *Am. J. Respir. Crit. Care Med.* 2002, 166, 954-960; and Churg, A. et al. *Am. J. Respir. Grit. Care Med.* 2003, 168, 199-207, both of which are incorporated herein by reference in their entireties). Thus, HNE may play a role both in matrix destruction and in amplifying inflammatory responses in chronic respiratory diseases where neutrophil influx is a characteristic feature. Indeed, HNE is believed to play a role in several pulmonary diseases, including COPD, cystic fibrosis (CF), acute respiratory distress syndrome (ARDS), pulmonary emphysema, pneumonia and lung fibrosis. It is also implicated in several cardiovascular diseases in which tissue remodelling is involved, for example, in heart failure and the generation of ischaemic tissue injury following acute myocardial infarction.

COPD is an umbrella term encompassing three different pathological conditions, all of which contribute to limitation of airflow: chronic bronchitis, emphysema, and small-airway disease. Generally all three will exist to varying extents in patients presenting with COPD, and all three may be due to neutrophil-mediated inflammation, as supported by the increased number of neutrophils observed in bronchoalveolar leakage (BAL) fluids of COPD patients (see Thompson, A. B.; Daughton, D.; et al. *Am. Rev. Respir. Dis.* 1989, 140, 1527-1537, which is incorporated herein by reference in its entirety). The major pathogenic determinant in COPD has long been considered to be the protease-anti-protease balance (also known as the "elastase:anti-elastase hypothesis"), in which an imbalance of HNE and endogenous antiproteases such as al-antitrypsin ($\alpha_1$-AT), secretory leukocyte protease inhibitor (SLPI) and pre-elafin leads to the various inflammatory disorders of COPD. Individuals that have a genetic deficiency of the protease inhibitor $\alpha$1-antitrypsin develop emphysema that increases in severity over time (see Laurrell, C. B.; Erikkson, S *Scand. J. Clin. Invest.* 1963 15, 132-140, which is incorporated herein by reference in its entirety). An excess of HNE is therefore destructive, leading to the breakdown of pulmonary morphology with loss of elasticity and destruction of alveolar attachments of airways in the lung (emphysema) whilst simultaneously increasing microvascular permeability and mucus hypersecretion (chronic bronchitis).

Several human neutrophil inhibitors have been disclosed so far in the art. In particular, International Patent Applications WO2011/110858, WO2011/110859, and WO 2014/009425, all of which are incorporated herein by reference in their entireties, describe some pyrimidine derivatives having human neutrophil elastase inhibitory properties and their use in therapy.

Although several HNE inhibitors have been disclosed so far as above reported, there is still a need for further HNE inhibitors. Particularly, there is still a need for further HNE inhibitors endowed with a high potency for HNE enzyme inhibition. Particularly advantageous would also be the identification of further HNE inhibitors endowed with a high potency for HNE enzyme inhibition and which would show an appropriate developability profile as an inhalation treatment or oral treatment.

SUMMARY OF THE INVENTION

Accordingly, it is one object of the present invention to provide novel HNE inhibitors.

It is another object of the present invention to provide novel HNE inhibitors endowed with a high potency for HNE enzyme inhibition.

It is another object of the present invention to provide novel pharmaceutical compositions which contain such a HNE inhibitor.

It is another object of the present invention to provide novel methods of treating and/or preventing certain diseases and conditions by administering such a HNE inhibitor.

These and other objects, which will become apparent during the following detailed description, have been achieved by the inventors' discovery that the compounds of formula (I) described below are inhibitors of HNE and are useful in the treatment of diseases or conditions in which HNE activity plays a part.

DETAILED DESCRIPTION OF THE PREFERRED EMBODIMENTS

According to the present invention there are provided compounds of formula (I):

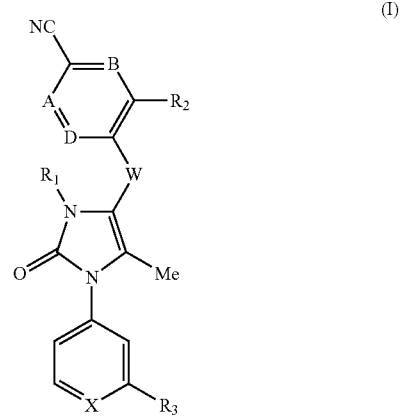

wherein
A is —CH or —N—;
B is —CH or —N—;
D is —CH or —N—;

X is —CH or —N—;

$R_3$ is —$CF_3$, $CHF_2$, or halogen;

W is a 5- or 6-membered heteroaryl ring, optionally substituted with one or more substituents selected from —CN, —$NO_2$, —$O(C_1-C_6)$alkyl, —$(C_1-C_3)$alkyl-O—$(C_1-C_6)$alkyl, —$(C_1-C_3)$alkylamino, —$(C_3-C_8)$cycloalkyl, —OH, $(C_1-C_3)$ alkyl, halo, —$CF_3$, and —$SO_2(C_1-C_4)$alkyl;

$R_1$ is H or is selected from the group consisting of —$C(O)$ $R_4$, —$(CH_2)_t$—$(CHR_6)_n$—$R_4$, —$(CH_2)_t$—$(CHR_6)_n S(O_2)$— $NR_4R_5$, —$S(O_2)$—$R_4$, —$(CH_2)_t$—$(CHR_6)_n$—$C(O)$— $NR_4R_5$, and —$(CH_2)_t$—$(CHR_6)_n$—$C(O)O$—$R_4$, $R_4$ is H or is selected in the group consisting of —$(C_1-C_6)$ alkyl, —$(C_2-C_6)$alkyl-$NR_7R_8$, —$(C_2-C_6)$alkyl-$N^+R_7R_8R_9$, —$(C_2-C_6)$alkyl-O—$(C_1-C_4)$alkyl, —$(C_2-C_6)$alkyl-$S(O_2)$ $(C_1-C_4)$alkyl, —$(CH_2)_t$-aryl, —$(CH_2)_t$—$(C_3-C_8)$cycloalkyl, —$(CH_2)_t$—$(C_3-C_8)$heterocycloalkyl, and —$(CH_2)_t$-heteroaryl, optionally substituted with one or more substituents selected from —CN, —$NO_2$, —$O(C_1-C_6)$alkyl, —$(C_1-C_3)$ alkyl-O—$(C_1-C_6)$alkyl, —$(C_1-C_3)$alkylamino, —$(C_3-C_8)$cycloalkyl, —OH, $(C_1-C_3)$alkyl, halo, —$CF_3$, and —$SO_2(C_1-C_4)$alkyl;

n is 0 or an integer selected from 1, 2 or 3;

t is 0 or an integer selected from 1, 2 or 3;

$R_5$ is H or —$(C_1-C_6)$alkyl;

$R_6$ is H, —$(C_1-C_6)$alkyl, —$CF_3$, or —$CHF_2$;

$R_7$ is H or —$(C_1-C_6)$alkyl;

$R_8$ is H or —$(C_1-C_6)$alkyl;

$R_9$ is H or —$(C_1-C_6)$alkyl;

or, alternatively $R_4$ and $R_5$, together with the nitrogen atom they are linked to, may form a $(C_3-C_8)$heterocycloalkyl or heteroaryl ring system, optionally substituted with one or more substituents selected from —CN, —$NO_2$, —$O(C_1-C_6)$ alkyl, —$(C_1-C_3)$alkyl-O—$(C_1-C_6)$alkyl, —$(C_1-C_3)$alkylamino, —$(C_3-C_8)$cycloalkyl, —OH, $(C_1-C_3)$alkyl, halo, —$CF_3$, and —$SO_2(C_1-C_4)$alkyl, wherein the heteroatoms of the $(C_3-C_8)$heterocycloalkyl or heteroaryl ring system are maximum three and selected from —N, —NH, —O, —S—, and —$SO_2$;

$R_2$ is H or is selected from the group consisting of, —SMe, —$S(O)R_B$, —$S(O_2)R_7$, and halogen;

and pharmaceutically acceptable salts thereof.

Compounds of the present invention may be used in the treatment or prevention of diseases in which HNE is implicated, for example COPD, bronchiectasis, chronic bronchitis, lung fibrosis, pneumonia, ARDS, pulmonary emphysema, smoking-induced emphysema, and CF.

Hence other aspects of the present invention are (i) pharmaceutical compositions comprising a compound of the present invention and one or more pharmaceutically acceptable carriers or excipients; and (ii) the use of a compound of the invention for the manufacture of a medicament for the treatment or prevention of a disease or condition in which HNE is implicated.

Unless otherwise specified, the term "substituted" as applied to any moiety herein means substituted with one or more substituents selected from —CN, —$NO_2$, —$O(C_1-C_6)$ alkyl, —$(C_1-C_3)$alkyl-O—$(C_1-C_6)$alkyl, —$(C_1-C_3)$alkylamino, —$(C_3-C_8)$cycloalkyl, —OH, $(C_1-C_3)$alkyl, halo (including fluoro, bromo and chloro), —$CF_3$ and —$SO_2(C_1-C_4)$ alkyl.

As used herein, the term "halogen" includes fluorine, chlorine, bromine, and iodine atoms.

As used herein, the term "$(C_x-C_y)$alkyl" wherein x and y are integers, refers to a straight or branched chain alkyl radical having from x to y carbon atoms. Thus when x is 1 and y is 6, for example, the term includes methyl, ethyl, n-propyl, isopropyl, n-butyl, isobutyl, sec-butyl, t-butyl, n-pentyl and n-hexyl.

The term "$(C_x-C_y)$cycloalkyl", wherein x and y are integers, refers to saturated monocyclic, bicyclic or tricyclic hydrocarbon groups containing from x to y ring carbon atoms, as appropriate, and wherein a carbon atom can be replaced by a group CO. Examples include cyclopropyl, cyclobutyl, cyclopentyl, cyclohexyl, cycloheptyl, and adamantyl.

As used herein, the term "heterocycloalkyl" relates to a saturated mono-, bi-, or tri-cyclic non-aromatic radical containing one or more heteroatoms selected from S, SO, $SO_2$, N, NH, and O and wherein a carbon atom may be replaced by a group CO. In the case of bicyclic heterocyclic systems, included within the scope of the term are fused, Spiro and bridged bicyclic systems, such as for example a quinuclidine ring. In particular, the term "$(C_x-C_y)$heterocycloalkyl" refers to monocyclic $(C_x-C_y)$cycloalkyl groups, in which at least one ring carbon atom is replaced by a heteroatom (e.g. N, NH, S, SO, $SO_2$, or O). Examples of $(C_x-C_y)$heterocycloalkyl include pyrrolidinyl, thiazolidinyl, piperazinyl, piperidinyl, morpholinyl, and thiomorpholinyl.

As used herein, the term "aryl" refers to a mono- or bi-cyclic carbocyclic aromatic radical, and includes radicals having two monocyclic carbocyclic aromatic rings which are directly linked by a covalent bond. Illustrative of such radicals are phenyl, biphenyl, and naphthyl.

As used herein, the term "heteroaryl" refers to a mono- or bi-cyclic aromatic radical containing one or more heteroatoms selected from S, N and O, and includes radicals having two such monocyclic rings, or one such monocyclic ring and one monocyclic aryl ring, which are fused through a common bond. Illustrative examples of 5,6-membered heteroaryl are thienyl, furyl, pyrrolyl, imidazolyl, thiazolyl, isothiazolyl, pyrazolyl, oxazolyl, isoxazolyl, isothiazolyl, triazolyl, thiadiazolyl, oxadiazolyl, pyridinyl, pyridazinyl, pyrimidinyl, pyrazinyl, and triazinyl. Illustrative examples of 8-10-membered heteroaryl are benzothienyl, benzofuryl, benzimidazolyl, benzothiazolyl, benzisothiazolyl, benzoxazolyl, benzisoxazolyl, benzotriazolyl, indolyl, and indazolyl.

The term "salt" includes base addition and acid addition salts.

The term "pharmaceutically acceptable salts" refers to derivatives of compounds of formula (I) wherein the parent compound is suitably modified by converting any of the free acid or basic groups, if present, into the corresponding addition salt with any base or acid conventionally intended as being pharmaceutically acceptable.

Compounds of the present invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl) amino-methane, L-arginine, L-lysine, N-ethyl piperidine, dibenzylamin,e and the like. Those compounds which are basic can form salts, including pharmaceutically acceptable salts with inorganic acids, e.g. with hydrohalic acids such as hydrochloric or hydrobromic acids, sulfuric acid, nitric acid or phosphoric acid, and the like, and with organic acids e.g. with acetic, tartaric, succinic, fumaric, maleic, malic, salicylic, citric, methanesulfonic, p-toluenesulfonic, benzoic, benzenesulfonic, glutamic, lactic, and mandelic acids, and the like. Those compounds which have quaternary nitrogen can also form quaternary salts with a pharmaceutically acceptable counter-ion such as chloride, bromide, acetate, formate, p-toluenesulfonate, succinate, hemi-succinate, naphthalene bis-sulfonate, methanesulfonate, xinafoate, and the like.

Where the compounds of the present invention have at least one stereogenic center, they may exist as enantiomers. When the compounds according to the present invention possess two or more stereogenic centers, they may additionally exist as diastereoisomers. It is to be understood that all such isomers and mixtures thereof in any proportion are encompassed within the scope of the present invention.

Accordingly, as used herein, a compound of the present invention can be in the form of one of the possible isomers, rotamers, atropisomers, tautomers, or mixtures thereof, for example, as substantially pure geometric (cis or trans) isomers, diastereoisomers, optical isomers (antipodes), racemates or mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound as defined in the first aspect. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such a compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds as defined in the first aspect can generally be prepared by conventional techniques known to those skilled in the art or by processes analogous to those described using appropriate isotopically-labeled reagents in place of the non-labeled reagents previously employed.

It is to be understood that all preferred groups or embodiments described here below for compounds of formula (I) can be combined among each other and apply mutatis mutandis.

In one embodiment, for compounds of formula (I) A, B, D and X are —CH.

In one embodiment, W is a 5-membered heteroaryl ring.

In another preferred embodiment, W is selected from the group consisting of pyrazolyl, imidazolyl, and tiazolyl.

In one preferred embodiment, $R_3$ is —$CF_3$.

In one preferred embodiment, $R_2$ is H.

In one preferred embodiment, $R_2$ is —$S(O_2)R_7$ wherein $R_7$ is H or —($C_1$-$C_6$)alkyl. In one preferred embodiment, $R_2$ is halogen.

In another preferred embodiment, $R_1$ is H.

In another preferred embodiment, $R_1$ is selected from the list consisting of —C(O)$R_4$; —($CH_2$)$_t$—($CHR_6$)$_n$—$R_4$; —($CH_2$)$_t$—($CHR_6$)$_n$S(O$_2$)—$NR_4R_5$; —S(O$_2$)—$R_4$; —($CH_2$)$_t$—($CHR_6$)$_n$—C(O)—$NR_4R_5$, and —($CH_2$)$_t$—($CHR_6$)$_n$—C(O)O—$R_4$.

In another preferred embodiment, $R_1$ is —($CH_2$)$_t$—($CHR_6$)$_n$—$R_4$ wherein $R_4$ is H or is selected from the group consisting of —($C_1$-$C_6$)alkyl, —($C_2$-$C_6$)alkyl-$NR_7R_8$ and —($C_2$-$C_6$)alkyl-$S(O_2)$($C_1$-$C_4$)alkyl; wherein $R_7$ is H or —($C_1$-$C_6$)alkyl; $R_8$ is H or —($C_1$-$C_6$)alkyl; t is 0 or an integer selected from 1, 2 or 3; n is 0 or an integer selected from 1, 2 or 3.

In another preferred embodiment, $R_1$ is —($CH_2$)$_t$—($CHR_6$)$_n$S(O$_2$)—$NR_4R_5$ wherein $R_4$ is H or is selected in the group consisting of —($C_1$-$C_6$)alkyl and —($C_3$-$C_8$)cycloalkyl; $R_5$ is H or —($C_1$-$C_6$)alkyl; t is 0 or an integer selected from 1, 2 or 3; n is 0 or an integer selected from 1, 2 or 3.

In another preferred embodiment, $R_1$ is —($CH_2$)$_t$—($CHR_6$)$_n$—C(O)O—$R_4$ wherein $R_4$ is H or —($C_1$-$C_6$)alkyl, optionally substituted with one or more substituents selected from —CN, —$NO_2$, —O($C_1$-$C_6$)alkyl, —OH, ($C_1$-$C_3$)alkyl, halo, and —$CF_3$; $R_6$ is H, —($C_1$-$C_6$)alkyl, —$CF_3$ or —$CHF_2$; t is 0 or an integer selected from 1, 2 or 3; n is 0 or an integer selected from 1, 2 or 3.

In another preferred embodiment, $R_1$ is —C(O)$R_4$, wherein $R_4$ is H or —($C_1$-$C_6$)alkyl, optionally substituted with one or more substituents selected from CN, —$NO_2$, —O($C_1$-$C_6$)alkyl, —OH, halo, and —$CF_3$.

In another preferred embodiment, $R_1$ is —($CH_2$)$_t$—($CHR_6$)$_n$—C(O)—$NR_4R_5$ wherein $R_4$ is H or is selected from the group consisting of —($C_1$-$C_6$)alkyl, optionally substituted with one or more groups selected from —O($C_1$-$C_6$)alkyl, —($C_1$-$C_3$)alkylamino, —$SO_2$($C_1$-$C_4$)alkyl and —OH, or $R_4$ is selected from the group consisting of —($CH_2$)$_t$—($C_3$-$C_8$)cycloalkyl, —($CH_2$)$_t$—($C_3$-$C_8$)heterocycloalkyl, —($C_2$-$C_6$)alkyl-$NR_7R_8$, —($CH_2$)$_t$-aryl, —($CH_2$)$_t$-heteroaryl, and —($C_2$-$C_6$)alkyl-$N^+R_7R_8R_9$, optionally substituted with one or more groups selected from —($C_1$-$C_6$)alkyl, —$SO_2$($C_1$-$C_4$)alkyl, and —OH; $R_5$ is H or —($C_1$-$C_6$)alkyl; or wherein alternatively $R_4$ and $R_5$, together with the nitrogen atom they are linked to, may form a ($C_3$-$C_8$)heterocycloalkyl or heteroaryl ring system, optionally substituted with one or more substituents selected from —OH and ($C_1$-$C_3$)alkyl, wherein the heteroatoms of the ($C_3$-$C_8$)heterocycloalkyl or heteroaryl ring system are maximum three and selected from —N, —NH, —O, —S—, and —$SO_2$; $R_6$ is H, —($C_1$-$C_6$)alkyl, —$CF_3$ or —$CHF_2$; $R_7$ is H or —($C_1$-$C_6$)alkyl; $R_8$ is H or —($C_1$-$C_6$)alkyl; t is 0 or an integer selected from 1, 2 or 3; n is 0 or an integer selected from 1, 2 or 3.

In another preferred embodiment, $R_1$ is —S(O$_2$)—$R_4$ wherein $R_4$ is H or is selected from the group consisting of —($CH_2$)$_t$—($C_3$-$C_8$)cycloalkyl and —($C_1$-$C_6$)alkyl; t is 0 or an integer selected from 1, 2 or 3.

In one embodiment, for compounds of formula (I), a compound of the present invention is selected from the group consisting of

| Ex. | Chemical name |
|---|---|
| 1 | 4-(5-{5-Methyl-2-oxo-1-[3-(trifluoromethyl)phenyl]-2,3-dihydro-1H-imidazol-4-yl}-1H-pyrazol-1-yl)benzonitrile |
| 2 | 4-(5-{5-Methyl-3-[3-(methylsulfonyl)propyl]-2-oxo-1-[3-(trifluoromethyl)-phenyl]-2,3-dihydro-1H-imidazol-4-yl}-1H-pyrazol-1-yl)benzonitrile |
| 3 | 4-(5-{3,5-Dimethyl-2-oxo-1-[3-(trifluoromethyl)phenyl]-2,3-dihydro-1H-imidazol-4-yl}-1H-pyrazol-1-yl)benzonitrile |
| 4 | Ethyl-5-[1-(4-cyanophenyl)-1H-pyrazol-5-yl]-4-methyl-2-oxo-3-[3-(trifluoromethyl)phenyl]-2,3-dihydro-1H-imidazole-1-carboxylate |

-continued

| Ex. | Chemical name |
|---|---|
| 5 | 4-(5-{3-Acetyl-5-methyl-2-oxo-1-[3-(trifluoromethyl)phenyl]-2,3-dihydro-1H-imidazol-4-yl}-1H-pyrazol-1-yl)benzonitrile |
| 6 | 5-[1-(4-Cyanophenyl)-1H-pyrazol-5-yl]-N-ethyl-4-methyl-2-oxo-3-[3-(trifluoromethyl)phenyl]-2,3-dihydro-1H-imidazole-1-carboxamide |
| 7 | 5-[1-(4-Cyanophenyl)-1H-pyrazol-5-yl]-N-(2-hydroxyethyl)-4-methyl-2-oxo-3-[3-(trifluoromethyl)phenyl]-2,3-dihydro-1H-imidazole-1-carboxamide |
| 8 | 5-[1-(4-Cyanophenyl)-1H-pyrazol-5-yl]-N-(3-hydroxypropyl)-4-methyl-2-oxo-3-[3-(trifluoromethyl)phenyl]-2,3-dihydro-1H-imidazole-1-carboxamide |
| 9 | 5-[1-(4-Cyanophenyl)-1H-pyrazol-5-yl]-N-[3-(dimethylamino)propyl]-4-methyl-2-oxo-3-[3-(trifluoromethyl)phenyl]-2,3-dihydro-1H-imidazole-1-carboxamide |
| 10 | 4-(5-{3-Butanoyl-5-methyl-2-oxo-1-[3-(trifluoromethyl)phenyl]-2,3-dihydro-1H-imidazol-4-yl}-1H-pyrazol-1-yl)benzonitrile |
| 11 | 5-[1-(4-Cyanophenyl)-1H-pyrazol-5-yl]-N-(2-methoxyethyl)-4-methyl-2-oxo-3-[3-(trifluoromethyl)phenyl]-2,3-dihydro-1H-imidazole-1-carboxamide |
| 12 | 5-[1-(4-Cyanophenyl)-1H-pyrazol-5-yl]-N-[2-(dimethylamino)ethyl]-4-methyl-2-oxo-3-[3-(trifluoromethyl)phenyl]-2,3-dihydro-1H-imidazole-1-carboxamide |
| 13 | 5-[1-(4-Cyanophenyl)-1H-pyrazol-5-yl]-4-methyl-N-[2-(methylsulfonyl)ethyl]-2-oxo-3-[3-(trifluoromethyl)phenyl]-2,3-dihydro-1H-imidazole-1-carboxamide |
| 14 | 5-[1-(4-Cyanophenyl)-1H-pyrazol-5-yl]-4-methyl-2-oxo-N-(tetrahydrofuran-3-yl)-3-[3-(trifluoromethyl)phenyl]-2,3-dihydro-1H-imidazole-1-carboxamide |
| 15 | 5-[1-(4-Cyanophenyl)-1H-pyrazol-5-yl]-4-methyl-2-oxo-N-[(3S)-tetrahydrfuran-3-yl]-3-[3-(trifluoromethyl)phenyl]-2,3-dihydro-1H-imidazole-1-carboxamide |
| 16 | 5-[1-(4-Cyanophenyl)-1H-pyrazol-5-yl]-4-methyl-2-oxo-N-[(3R)-tetrahydrofuran-3-yl]-3-[3-(trifluoromethyl)phenyl]-2,3-dihydro-1H-imidazole-1-carboxamide |
| 17 | 5-[1-(4-Cyanophenyl)-1H-pyrazol-5-yl]-4-methyl-N-[(1-methyl-1H-pyrazol-3-yl)methyl]-2-oxo-3-[3-(trifluoromethyl)phenyl]-2,3-dihydro-1H-imidazole-1-carboxamide |
| 18 | Methyl-5-[1-(4-cyanophenyl)-1H-pyrazol-5-yl]-4-methyl-2-oxo-3-[3-(trifluoromethyl)phenyl]-2,3-dihydro-1H-imidazole-1-carboxylate |
| 19 | 4-(5-{5-Methyl-2-oxo-3-pentanoyl-1-[3-(trifluoromethyl)phenyl]-2,3-dihydro-1H-imidazol-4-yl}-1H-pyrazol-1-yl)benzonitrile |
| 20 | tert-Butyl-{5-[1-(4-cyanophenyl)-1H-pyrazol-5-yl]-4-methyl-2-oxo-3-[3-(trifluoromethyl)phenyl]-2,3-dihydro-1H-imidazol-1-yl} acetate |
| 21 | 5-[1-(4-Cyanophenyl)-1H-pyrazol-5-yl]-N-ethyl-N,4-dimethyl-2-oxo-3-[3-(trifluoromethyl)phenyl]-2,3-dihydro-1H-imidazole-1-carboxamide |
| 22 | {5-[1-(4-Cyanophenyl)-1H-pyrazol-5-yl]-4-methyl-2-oxo-3-[3-(trifluoromethyl)phenyl]-2,3-dihydro-1H-imidazol-1-yl}acetic acid |
| 23 | 2-{5-[1-(4-Cyanophenyl)-1H-pyrazol-5-yl]-4-methyl-2-oxo-3-[3-(trifluoromethyl)phenyl]-2,3-dihydro-1H-imidazol-1-yl}-N-methylacetamide |
| 24 | Benzenesulfonate 3-[({5-[1-(4-cyanophenyl)-1H-pyrazol-5-yl]-4-methyl-2-oxo-3-[3-(trifluoromethyl)phenyl]-2,3-dihydro-1H-imidazol-1-yl} carbonyl)amino]-N,N,N-trimethylpropan-1-aminium |
| 25 | Benzenesulfonate 2-[({5-[1-(4-cyanophenyl)-1H-pyrazol-5-yl]-4-methyl-2-oxo-3-[3-(trifluoromethyl)phenyl]-2,3-dihydro-1H-imidazol-1-yl}carbonyl)amino]-N,N,N-trimethylethanaminium |
| 26 | 4-(5-{3-Butyl-5-methyl-2-oxo-1-[3-(trifluoromethyl)phenyl]-2,3-dihydro-1H-imidazol-4-yl}-1H-pyrazol-1-yl)benzonitrile |
| 27 | 4-(5-{5-Methyl-3-(methylsulfonyl)-2-oxo-1-[3-(trifluoromethyl)phenyl]-2,3-dihydro-1H-imidazol-4-yl}-1H-pyrazol-1-yl)benzonitrile |
| 28 | 4-{5-[5-Methyl-3-(1-methyl-butyl)-2-oxo-1-(3-trifluoromethyl-phenyl)-2,3-dihydro-1H-imidazol-4-yl]pyrazol-1-yl}-benzonitrile |
| 29 | 4-{5-[3-(2-Dimethylamino-ethyl)-5-methyl-2-oxo-1-(3-trifluoromethylphenyl)-2,3-dihydro-1H-imidazol-4-yl]-pyrazol-1-yl}-benzonitrile |
| 30 | 4-{5-[3-(3-Dimethylamino-propyl)-5-methyl-2-oxo-1-(3-trifluoromethylphenyl)-2,3-dihydro-1H-imidazol-4-yl]-pyrazol-1-yl}-benzonitrile |
| 31 | 4-{5-[5-Methyl-2-oxo-3-(propane-1-sulfonyl)-1-(3-trifluoromethylphenyl)-2,3-dihydro-1H-imidazol-4-yl]-pyrazol-1-yl}-benzonitrile |
| 32 | 4-{5-[3-Cyclopropanesulfonyl-5-methyl-2-oxo-1-(3-trifluoromethylphenyl)-2,3-dihydro-1H-imidazol-4-yl]-pyrazol-1-yl}-benzonitrile |
| 33 | 5-[2-(4-Cyano-phenyl)-2H-pyrazol-3-yl]-4-methyl-2-oxo-3-(3-trifluoromethylphenyl)-2,3-dihydro-imidazole-1-sulfonic acid ethylamide |
| 34 | 5-[2-(4-Cyano-phenyl)-2H-pyrazol-3-yl]-4-methyl-2-oxo-3-(3-trifluoromethylphenyl)-2,3-dihydro-imidazole-1-sulfonic acid cyclopentylamide |
| 35 | 5-[2-(4-Cyano-phenyl)-2H-pyrazol-3-yl]-4-methyl-2-oxo-3-(3-trifluoromethylphenyl)-2,3-dihydro-imidazole-1-sulfonic acid cyclopropylamide |
| 36 | 4-{5-[5-Methyl-2-oxo-3-(2-oxo-2-pyrrolidin-1-yl-ethyl)-1-(3-trifluoromethylphenyl)-2,3-dihydro-1H-imidazol-4-yl]-pyrazol-1-yl}-benzonitrile |
| 37 | 2-[5-[2-(4-Cyano-phenyl)-2H-pyrazol-3-yl]-4-methyl-2-oxo-3-(3-trifluoromethyl-phenyl)-2,3-dihydro-imidazol-1-yl]-N,N-dimethyl-acetamide |
| 38 | 4-{5-[5-Methyl-3-[2-(4-methyl-piperazin-1-yl)-2-oxo-ethyl]-2-oxo-1-(3-trifluoromethyl-phenyl)-2,3-dihydro-1H-imidazol-4-yl]-pyrazol-1-yl}-benzonitrile |
| 39 | 2-[5-[2-(4-Cyano-phenyl)-2H-pyrazol-3-yl]-4-methyl-2-oxo-3-(3-trifluoromethyl-phenyl)-2,3-dihydro-imidazol-1-yl]-N-(3-dimethyl-aminopropyl)-acetamide formic acid salt |
| 40 | 2-[5-[2-(4-Cyano-phenyl)-2H-pyrazol-3-yl]-4-methyl-2-oxo-3-(3-trifluoromethyl-phenyl)-2,3-dihydro-imidazol-1-yl]-N-cyclobutyl-N-methyl-acetamide |
| 41 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid cyclobutylamide |
| 42 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid cyclopropylamide |
| 43 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid (1-ethanesulfonyl-piperidin-4-yl)-amide |
| 44 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid (tetrahydro-pyran-4-yl)-amide |
| 45 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid cyclopentylamide |
| 46 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid ((R)-1-methyl-pyrrolidin-3-yl)-amide |
| 47 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid ((S)-1-methyl-pyrrolidin-3-yl)-amide |
| 48 | Mixture of 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid ((3R,4S)-4-hydroxy-tetrahydro-furan-3-yl)-amide and 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid((3S,4R)-4-hydroxy-tetrahydro-furan-3-yl)-amide |
| 49 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid (pyridin-2-ylmethyl)-amide |
| 50 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid (pyridin-3-ylmethyl)-amide |
| 51 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid (pyridin-4-ylmethyl)-amide |
| 52 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid (pyrazin-2-ylmethyl)-amide |
| 53 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid ((1R,2R)-2-hydroxy-cyclopentyl)-amide |
| 54 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid (1-methyl-piperidin-4-ylmethyl)-amide |
| 55 | 3-Methanesulfonyl-4-{5-[5-methyl-2-oxo-1-(3-trifluoromethyl-phenyl)-2,3-dihydro-1H-imidazol-4-yl]-pyrazol-1-yl}-benzonitrile |
| 56 | 5-[2-(2-Bromo-4-cyano-phenyl)-2H-pyrazol-3-yl]-4-methyl-2-oxo-3-(3-trifluoromethyl-phenyl)-2,3-dihydro-imidazole-1-carboxylic acid cyclopentylamide |
| 57 | 5-[1-(2-Bromo-4-cyano-phenyl)-1H-pyrazol-3-yl]-4-methyl-2-oxo-3-(3-trifluoromethyl-phenyl)-2,3-dihydro-imidazole-1-carboxylic acid cyclopentylamide |

-continued

| Ex. | Chemical name |
|---|---|
| 58 | 5-[2-(4-Cyano-2-fluoro-phenyl)-2H-pyrazol-3-yl]-4-methyl-2-oxo-3-(3-trifluoromethyl-phenyl)-2,3-dihydro-imidazole-1-carboxylic acid cyclopentylamide |
| 59 | 4-[5'-Methyl-2'-oxo-1'-(3-trifluoromethyl-phenyl)-2',3'-dihydro-1'H-[2,4']biimidazolyl-1-yl]-benzonitrile |
| 60 | 1-(4-Cyano-phenyl)-5'-methyl-2'-oxo-1'-(3-trifluoromethyl-phenyl)-1',2'-dihydro-1H-[2,4']biimidazolyl-3'-carboxylic acid cyclopentylamide |
| 61 | 1-(4-Cyano-phenyl)-5'-methyl-2'-oxo-1'-(3-trifluoromethyl-phenyl)-1',2'-dihydro-1H[2,4']biimidazolyl-3'-carboxylic acid cyclobutylamide |
| 62 | 1-(4-Cyano-phenyl)-5¹-methyl-2'-oxo-1'-(3-trifluoromethyl-phenyl)-1',2'-dihydro-1H-[2,4']biimidazolyl-3'-carboxylic acid 4-methanesulfonyl-benzylamide |
| 63 | 5-[2-(4-Cyano-phenyl)-2H-[1,2,4]triazol-3-yl]-4-methyl-2-oxo-3-(3-trifluoromethyl-phenyl)-2,3-dihydro-imidazole-1-carboxylic acid cyclopentylamide | and pharmaceutically acceptable salts thereof.

The present invention is also directed to a process for the preparation of a compound of formula (I):

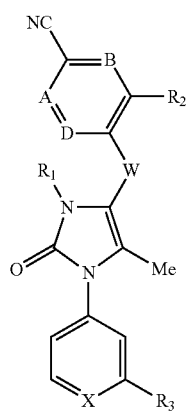

by reacting a compound of formula (IV):

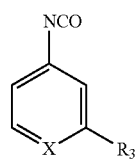

with prop-2-ynylamine to obtain a compound of formula (V):

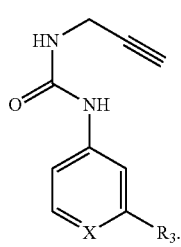

The present invention is also directed to a process for the preparation of a compound of formula (I) by reacting a compound of formula (V) following treatment with a base to obtain a compound of formula (VI):

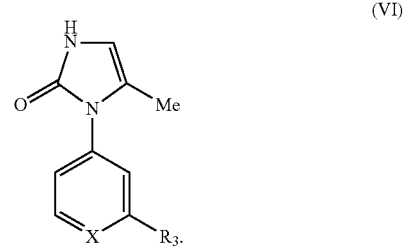

The present invention is also directed to a process for the preparation of a compound of formula (I) by reacting a compound of formula (VI) with an alkylating agent to obtain a compound of formula (VII):

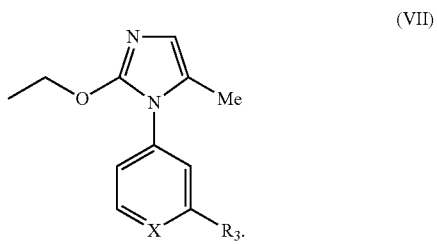

The present invention is also directed to a process for the preparation of a compound of formula (I) by reacting a compound of formula (VII) with a brominating agent to obtain a compound of formula (VIII):

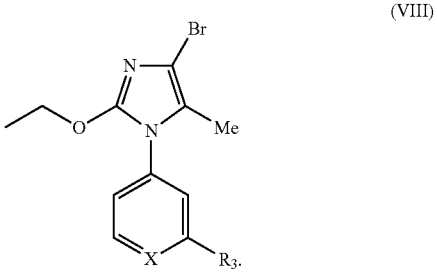

The present invention is also directed to a process for the preparation of a compound of formula (I) by reacting a compound of formula (VIII) with a compound of formula (IX):

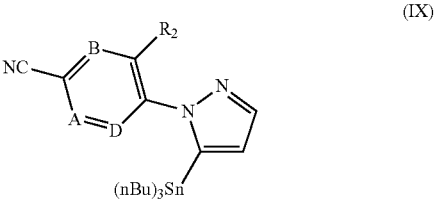

to obtain a compound of formula (II)'

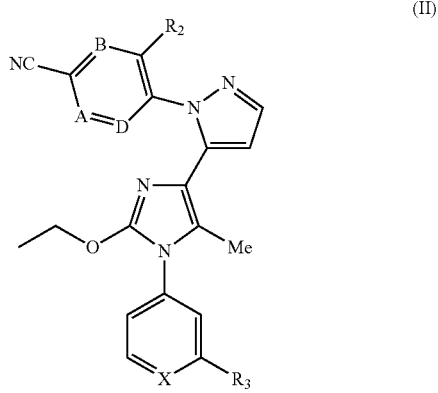

(II)

The present invention also provides pharmaceutical compositions comprising a compound of formula (I) together with one or more pharmaceutically acceptable carriers or excipients.

The present invention also provides pharmaceutical compositions comprising a compound of formula (I) which is adapted for oral administration or administration by the pulmonary route.

The present invention also provides compounds of formula (I) for the treatment of, or for use in the manufacture of a medicament for use in the treatment of, a disease or condition in which HNE is implicated.

The present invention also provides a method of treatment of a disease or condition in which HNE is implicated, comprising administering to a subject suffering such disease an effective amount of a compound of formula (I).

The present invention also provides a compound of formula (I) for use, or a method of treatment, wherein the disease or condition is COPD, bronchiectasis, chronic bronchitis, lung fibrosis, pneumonia, ARDS, pulmonary emphysema, smoking-induced emphysema, or cystic fibrosis.

The present invention also provides a compound of formula (I) for use, or a method of treatment, wherein the disease or condition is asthma, rhinitis, psoriasis, atopic dermatitis, non-atopic dermatitis, Crohn's disease, ulcerative colitis, or irritable bowel disease.

The therapeutic utility of the present compounds is pertinent to any disease that is known to be at least partially mediated by the action of human neutrophil elastase. For example, the present compounds may be beneficial in the treatment of COPD, CF, bronchiectasis, ARDS, pulmonary emphysema, pneumonia, and lung fibrosis.

Compounds of the present invention are useful for treatment of inflammatory respiratory disorders, for example asthma (mild, moderate or severe), steroid resistant asthma, bronchitis, COPD, CF, pulmonary edema, pulmonary embolism, pneumonia, pulmonary sarcoidosis, pulmonary emphysema, silicosis, pulmonary fibrosis, pulmonary hypertension, respiratory failure, ARDS, emphysema, chronic bronchitis, tuberculosis, aspergillosis and other fungal infections, hypersensitivity pneumonitis, vasculitic and thrombotic disorders of the lung vasculature, antitussive activity including treatment of chronic cough associated with inflammatory and secretory conditions of the airways, infection due to respiratory syncytial virus, influenza, coronavirus (including severe acute respiratory syndrome, SARS) and adenovirus, bronchiectasis, and lung cancer.

The present invention is also concerned with pharmaceutical formulations comprising, as an active ingredient, a compound of the invention. Other compounds may be combined with compounds of this invention for the prevention and treatment of inflammatory diseases of the lung. Thus the present invention is also concerned with pharmaceutical compositions for preventing and treating inflammatory diseases of the lung comprising a therapeutically effective amount of a compound of the invention and one or more other therapeutic agents.

Suitable therapeutic agents for a combination therapy with compounds of the present invention include: (1) a corticosteroid, for example budesonide, beclomethasone, beclomethasone (e.g., as the mono or the dipropionate ester), flunisolide, fluticasone (e.g. as the propionate or furoate ester), Ciclesonide, mometasone (e.g. as the furoate ester), mometasone desonide, rofleponide, hydrocortisone, prednisone, prednisolone, methyl prednisolone, naflocort, deflazacort, halopredone acetate, fluocinolone acetonide, fluocinonide, clocortolone, tipredane, prednicarbate, alclometasone dipropionate, halometasone, rimexolone, deprodone propionate, triamcinolone, betamethasone, fludrocoritisone, desoxycorticosterone, rofleponide, etiprednol dicloacetate and the like. Steroid drugs can additionally include steroids in clinical or pre-clinical development for respiratory diseases such as GW-685698, GW-799943, GSK 870086, QAE397, NCX-1010, NCX-1020, NO-dexamethasone, PL-2146, NS-126 (formerly ST-126). Steroid drugs can also additionally include next generation molecules in development with reduced side effect profiles such as selective glucocorticoid receptor agonists (SEGRAs), including ZK-216348 and AZD5423; (2) a β2-adrenoreceptor agonist, such as albuterol, bambuterol, terbutaline, fenoterol, formoterol, formoterol fumarate, salmeterol, salmeterol xinafoate, arformoterol, arformoterol tartrate, indacaterol (QAB-149), carmoterol, BI 1744 CL, GSK159797 (milveterol), GSK59790, GSK159802, GSK642444 (vilanterol), GSK678007, GSK96108, clenbuterol, procaterol, bitolterol, LAS100977 (abediterol), BI1744CL (olodaterol) and brodxaterol; (3) a leukotriene modulator, for example montelukast, zafirlukast or pranlukast; (4) anticholinergic agents, for example selective muscarinic-3 (M3) receptor antagonists such as ipratropium bromide, tiotropium, tiotropium bromide (Spiriva®), glycopyrronium bromide, aclidinium bromide, LAS34273, GSK656398, GSK233705, GSK 573719 (umeclidinium), LAS35201, QAT370 and oxytropium bromide; (5) phosphodiesterase-IV (PDE-IV) inhibitors, for example roflumilast, cilomilast or theophylline; (6) an antitussive agent, such as codeine or dextramorphan; and (7) a non-steroidal anti-inflammatory agent (NSAID), for example ibuprofen or ketoprofen; (8) a mucolytic, for example N acetyl cysteine or fudostein; (9) a expectorant/mucokinetic modulator, for example ambroxol, hypertonic solutions (e.g. saline or mannitol) or surfactant; (10) a peptide mucolytic, for example recombinant human deoxyribonoclease I (dornase-alfa and rhDNase) or helicidin; (11) antibiotics, for example azithromycin, tobramycin and aztreonam; and (12) p38 Mitogen Activated Protein (MAP) kinase inhibitors, such as GSK 856553 and GSK 681323; (12) inhibitors of Janus Kinases (JAK) such as CP-690550 or GLPG0634; (13) Spleen Tyrosine Kinase (SYK) inhibitors such as R406, R343 or PRT062607; (14) inhibitors of delta and/or gamma isoforms of Phosphatidylinositol 3-kinase (PI3K).; (15) anti-retroviral agents such as ribavirin, zanamivir or laninamivir; (16) PPAR-γ agonists such as pioglitazone and rosiglitazone.

In one aspect, the present invention provides for the use of inhaled administration of compounds of the present invention in combination with other anti-inflammatory drugs and bronchodilator drug combinations (i.e. triple combination product), including but not limited to salmeterol xinafoate/fluticasone propionate (Advair/Seretide®), vilanterol/fluticasone furoate (BREO ELLIPTA™), formoterol fumarate/budesonide (Symbicort®), formoterol fumarate/mometasone furoate, formoterol fumarate/beclometasone dipropionate (Foster), formoterol fumarate/fluticasone propionate (Fluti-Form®), Indacaterol/mometasone furoate, Indacaterol/QAE-397, GSK159797/GSK 685698, GSK159802/GSK 685698, GSK642444/GSK 685698, formoterol fumarate/ciclesonide, and arformoterol tartrate/ciclesonide.

In another aspect, the invention provides for the use of inhaled administration of compounds of the invention in combination with other bronchodilator drug combinations, particularly $\beta_2$ agonist/$M_3$ antagonist combinations (i.e. triple combination product), including but not limited to salmeterol xinafoate/tiotropium bromide, formoterol fumarate/tiotropium bromide, formoterol fumarate/glycopyrrolate (PT003), BI 1744 CL/tiotropium bromide, indacaterol/NVA237, indacterol/QAT-370, formoterol/LAS34273, umeclidinium/vilanterol (Anoro™), GSK159797/GSK 573719, GSK159802/GSK 573719, GSK642444/GSK 573719, GSK159797/GSK 233705, GSK159802/GSK 233705, and GSK642444/GSK 233705.

The weight ratio of the first and second active ingredients may be varied and will depend upon the effective dose of each ingredient. Generally, an effective dose of each will be used.

The magnitude of prophylactic or therapeutic dose of a compound of the present invention will, of course, vary with the nature of the severity of the condition to be treated and with the particular compound and its route of administration, and will generally be determined by clinical trial as required in the pharmaceutical art. It will also vary according to the age, weight and response of the individual patient. In general, the daily dose range will lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

Another aspect of the present invention provides pharmaceutical compositions which comprise a compound of the present invention and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by mixing a compound of the invention, additional active ingredient(s), and pharmaceutically acceptable excipients.

The pharmaceutical compositions of the present invention comprise a compound of the present invention as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Any suitable route of administration may be employed for providing a mammal, especially a human, with an effective dosage of a compound of the present invention. In therapeutic use, the active compound may be administered by any convenient, suitable or effective route. Suitable routes of administration are known, and include oral, intravenous, rectal, parenteral, topical, ocular, nasal, buccal, and pulmonary (by inhalation).

Compositions suitable for administration by inhalation are known, and may include carriers and/or diluents that are known for use in such compositions. The composition may contain 0.01 to 99% by weight of active compound. Preferably, a unit dose comprises the active compound in an amount of 1 µg to 10 mg.

The most suitable dosage level may be determined by any known suitable method. It will be understood, however, that the specific amount for any particular patient will depend upon a variety of factors, including the activity of the specific compound that is used, the age, body weight, diet, general health and sex of the patient, time of administration, the route of administration, the rate of excretion, the use of any other drugs, and the severity of the disease to be treated.

For delivery by inhalation, the active compound is preferably in the form of microparticles. They may be prepared by a variety of techniques, including spray-drying, freeze-drying and micronization.

By way of example, a composition of the present invention may be prepared as a suspension for delivery from a nebulizer or as an aerosol in a liquid propellant, for example for use in a pressurized metered dose inhaler (PMDI). Propellants suitable for use in a PMDI are known to the skilled person, and include CFC-12, HFA-134a, HFA-227, HCFC-22 (CC12F2) and HFA-152 (CH4F2 and isobutane).

In a preferred embodiment of the present invention, a composition of the present invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 µm.

In the case of an aerosol-based formulation, a preferred composition is:

| | |
|---|---|
| Compound of the present invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

Compounds of the present invention may be used in combination with other drugs that are used in the treatment/prevention/suppression or amelioration of the diseases or conditions for which present compounds are useful. Such other drugs may be administered, by a route and in an amount commonly used therefore, contemporaneously or sequentially with a compound of the invention. When a compound of the present invention is used contemporaneously with one or more other drugs, a pharmaceutical composition containing such other drugs in addition to the compound of the invention is preferred. Accordingly, the pharmaceutical compositions of the present invention include those that also contain one or more other active ingredients, in addition to a compound of the present invention.

The agents of the present invention may be administered in inhaled form. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk, Turbohaler® or the inhalers for example as described EP-A-0505321, which is incorporated herein by reference in its entirety).

Procedure for the Preparation of Compounds of Formula (I).

The present invention further provides a process for the preparation of a compound of formula (I) or a pharmaceutically acceptable salt or quaternary salt thereof as defined above. Compounds of the present invention (I) may be prepared according to routes illustrated below in Schemes A and B.

The skilled person may introduce, where appropriate, suitable variations to the conditions specifically described in the experimental in order to adapt the synthetic routes to the provision of further compounds of the invention. Such variations may include, but are not limited to, use of appropriate starting materials to generate different compounds, changes in the solvent and temperature of reactions, replacements of reactants with analogous chemical role, introduction or removal of protection/deprotection stages of functional groups sensitive to reaction conditions and reagents.

Also, introduction or removal of specific synthetic steps oriented to further functionalization of the chemical scaffold may be contemplated and is included within the scope of the present invention. Processes which can be used and are described and reported in the examples and schemes, should not be viewed as limiting the scope of the synthetic methods available for the preparation of the compounds of the invention.

Compounds used as starting materials or intermediates may be commercially available, their preparation may be specifically described in the literature, or they may be prepared according to methods available in the literature and well known to the person skilled in the art. In some instances, procedures for the preparation of intermediates or starting materials may be also provided in the experimental.

The process described is particularly advantageous as it is susceptible of being properly modulated, through any proper variant known to the skilled person, so as to obtain any of the desired compounds of the invention. Such variants are comprised within the scope of the present invention.

From all of the above, it should be clear to the skilled person that any of the described groups may be present as such or in any properly protected form.

In particular, functional groups present in the intermediate and compounds and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl, or benzyl esters or the like, which are well known to those skilled in the art (see, for a general reference, T. W. Green; Protective Groups in Organic Synthesis (Wiley, N. Y. 1981), which is incorporated herein by reference in its entirety).

Likewise, selective protection and deprotection of any of the said groups, for instance including carbonyl, hydroxyl, or amino groups, may be accomplished according to very well-known methods commonly employed in organic synthetic chemistry.

From all of the above, it should be clear to the skilled person that the above process, comprehensive of any variant thereof for the preparation of suitable compounds of the invention, may be conveniently modified so that to adapt the reaction conditions to the specific needs, for instance by choosing appropriate condensing agents, solvents, and protective groups, as the case may be.

In the following Schemes, for compounds of formula (II) to (XXIII) and (IB) to (IF), unless otherwise indicated, groups A, B, D, X, W, $R_1$ to $R_3$ have the same meanings as described for compounds of formula (I) above.

In one aspect of the present invention, a process for the preparation of compounds of the invention (IB), i.e. compounds of formula (I) wherein W=pyrazole (or as defined above), A, B, D, X and $R_1$ to $R_3$ are as defined above, may be prepared according to general synthetic routes reported in Scheme A here below.

Scheme A

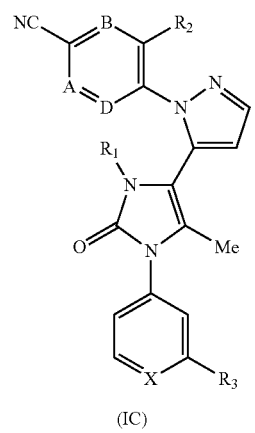

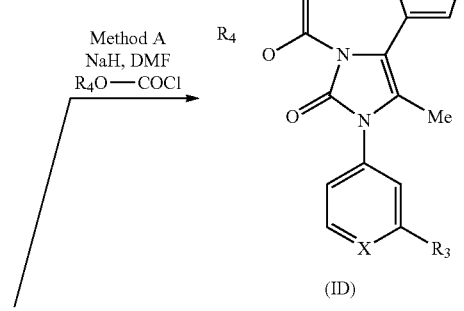

(IC)

(ID)

-continued

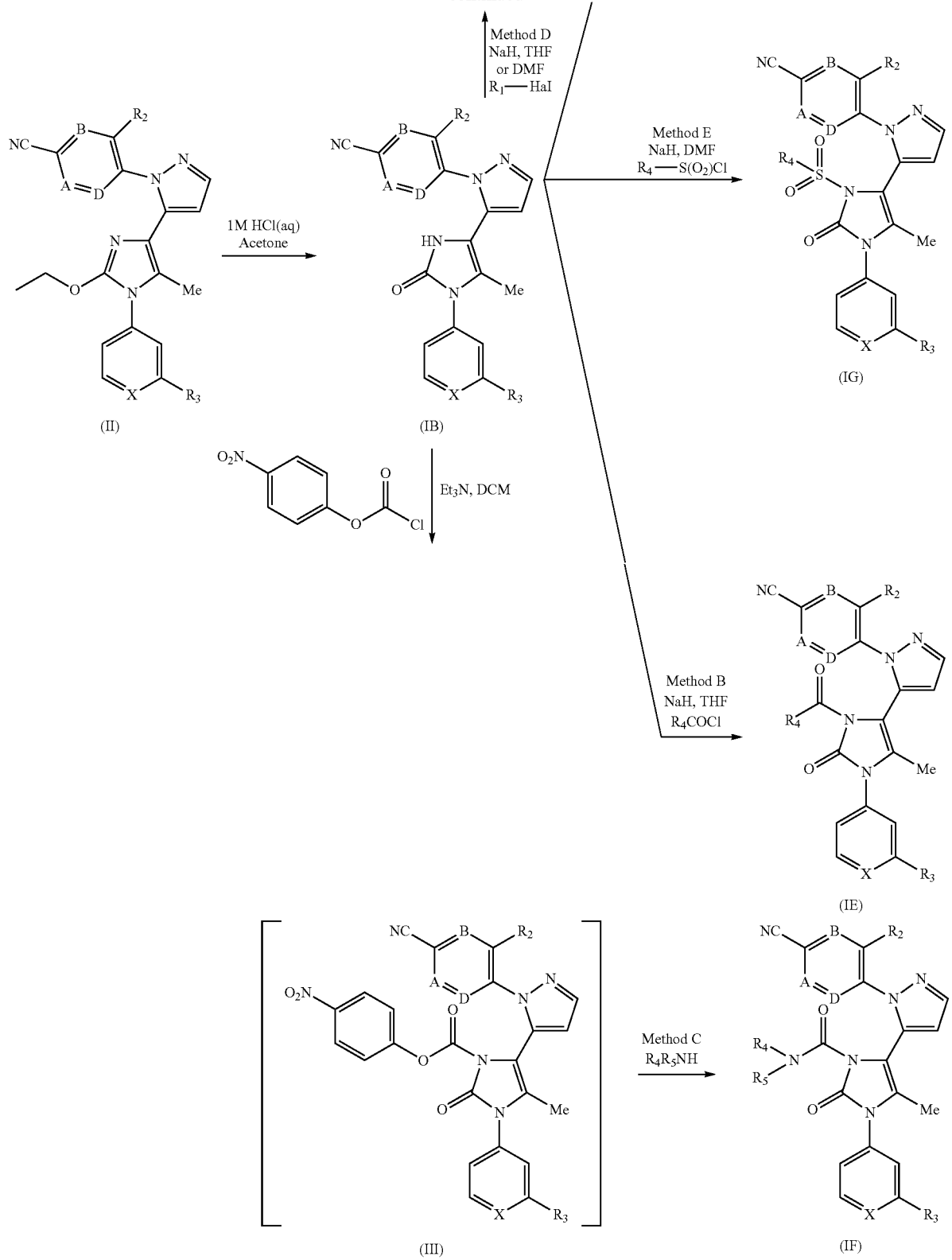

Compounds of formula (IB) may be prepared from compounds of formula (II) by reaction with an acid such as hydrochloric acid in a solvent such as acetone at temperature of from RT to 60° C. Compounds of formula (IB) may be converted into compounds of formula (IC) according to Method D, by reaction with an alkyl halide of formula $R_1$—Hal (Hal=Cl, Br, I) or $R_1$—X' wherein X' is an appropriate leaving group (e.g. X'=tosylate) in a solvent such as THF following addition of a base such as sodium hydride or lithium hexamethyldisilazide at a temperature of from 0° C. to 50° C. Alternatively, compounds of formula (IC) can be prepared according to Method F, by direct alkylation with $R_1$-Hal or $R_1$—X' at a temperature of up to 120° C. in a sealed vessel, followed by hydrolysis of the intermediate quaternary imidazolium compound with a base such as aqueous sodium hydroxide in a solvent such as acetonitrile.

Compounds of formula (ID), (IG), and (IE) can be prepared from compounds of formula (IB) by addition of a base such as sodium hydride followed by reaction with a chloroformate of formula $R_4CO_2Cl$, or $R_4SO_2Cl$ or acid chloride of formula $R_4COCl$, according to Methods A, E, and B respectively, in a suitable solvent such as THF or DMF at temperatures of from 0° C. to 60° C. Compounds of formula (IF) can be prepared from compounds of formula (IB) following the generation of the nitro-chloroformate intermediate (III) and reaction with a suitable amine $R_4R_5NH$, in a solvent such as DCM at a temperature of from 0° C. to 40° C.

Compounds of formula (II) can be prepared according to Scheme B below from compounds of formula (IV):

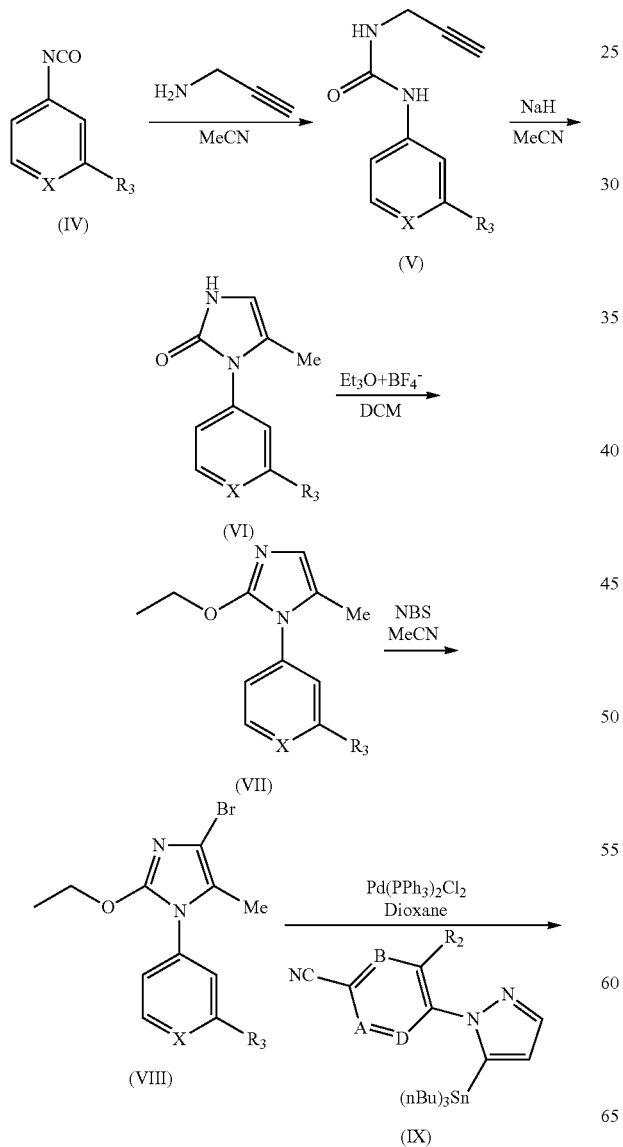

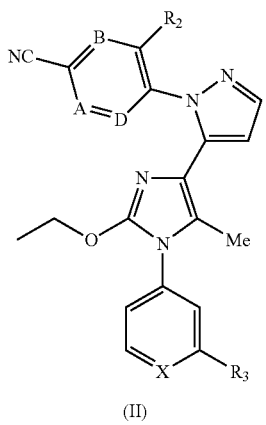

Compounds of formula (V) may be obtained from compounds of formula (IV) by reacting with prop-2-ynylamine in a suitable solvent such as DCM at a suitable temperature of between 0° C. and RT. Compounds of formula (VI) can be prepared from compounds of formula (V) following treatment with a suitable base such as sodium hydride in a suitable solvent such as acetonitrile or THF (or mixtures thereof). The conversion of compounds of formula (VI) to compounds of formula (VII) can be effected by reaction with a suitable alkylating agent such as trimethoxonium tetrafluoroborate, in a suitable solvent such as DCM at a suitable temperature of between 0° C. and RT. Compounds of formula (VIII) can be prepared from compounds of formula (VII) using a brominating agent such as N-bromosuccinimide or bromine in a suitable solvent such as acetonitrile at a suitable temperature of between 0° C. and RT. Compounds of formula (II) can be prepared from compounds of formula (VIII) using known C—C and C—N cross-coupling methodologies described in the literature using a suitably functionalized linking group "W" such as aryl, heteroaryl, cycloalkyl or heterocycloalkyl boronic acid/boronate ester, stannane or zincate. Typical reaction conditions consist of the use of an organometallic reactant such as 4-(5-tributylstannanyl-pyrazol-1-yl)-benzonitrile (IX) and a palladium source such as bis(triphenylphosphine)palladium (II) dichloride and a solvent such as dioxane at a temperature of between 50° C. and reflux or higher temperatures using microwave irradiation.

Compounds of formula (IB) and formula (XIII) can also be prepared according to Scheme C below from compounds of formula (VIII):

Scheme C

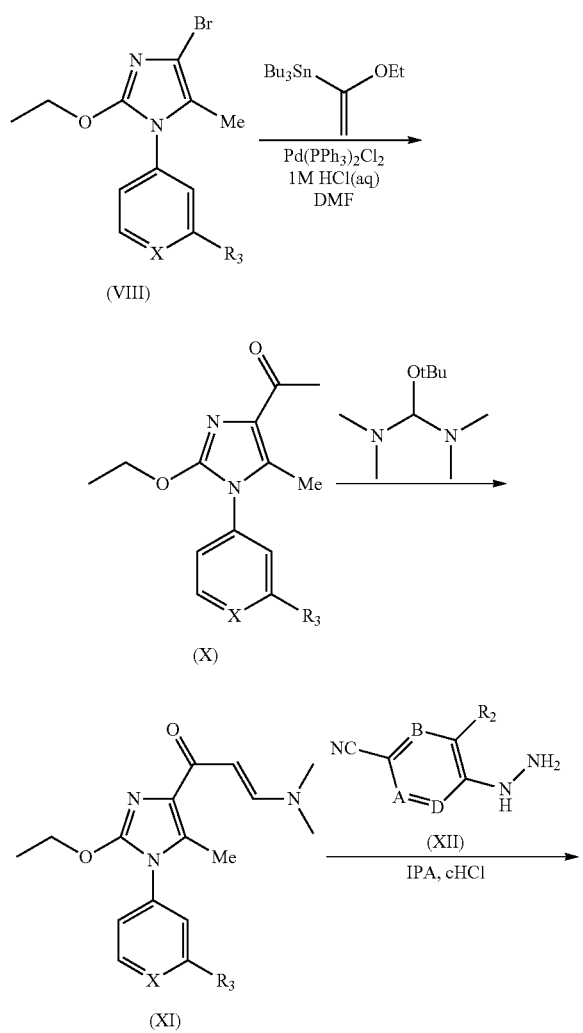

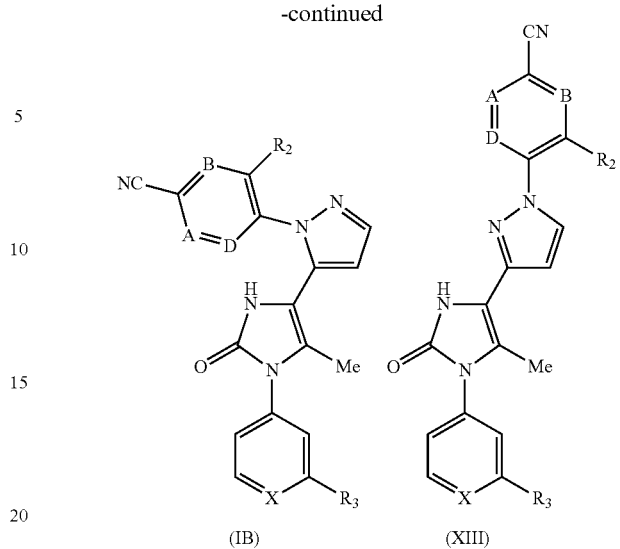

Compounds of formula (X) may be obtained from compounds of formula (VIII) by reacting with tributyl(1-ethoxyvinyl)tin in the presence of a suitable catalyst, for example bis(triphenylphosphine)palladium(II) dichloride, in a suitable solvent such as DMF containing an aqueous acid such as 1M hydrochloric at a suitable temperature between ambient and the boiling point of the solvent.

Compounds of formula (XI) may be obtained from compounds of formula (X) by reacting with a reagent such as Bredereck's reagent (tert-butoxy-bis(dimethylamino)-methane) or dimethylformamide-dimethylacetal at a suitable temperature between ambient and the boiling point of the solvent.

Compounds of formula (IB) and formula (XIII) may be obtained from compounds of formula (XI) by reacting with compounds of formula (XII) in a solvent such as IPA in the presence of an acid such as concentrated hydrochloric acid.

Compounds of formula (II), formula (XXII) and formula (XXIII) can also be prepared according to Scheme D below from compounds of formula (VIII):

Scheme D

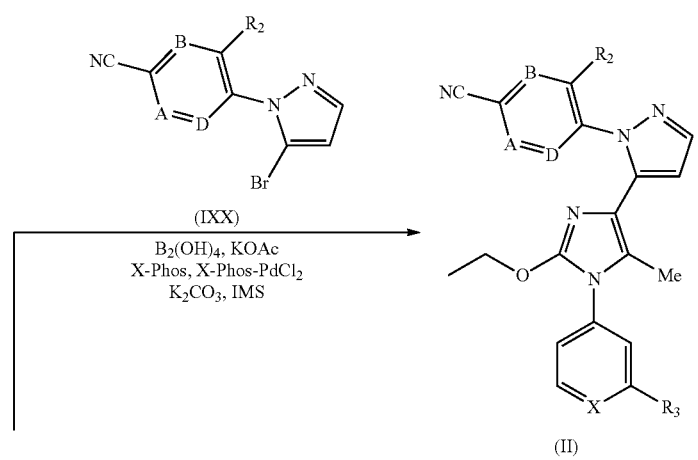

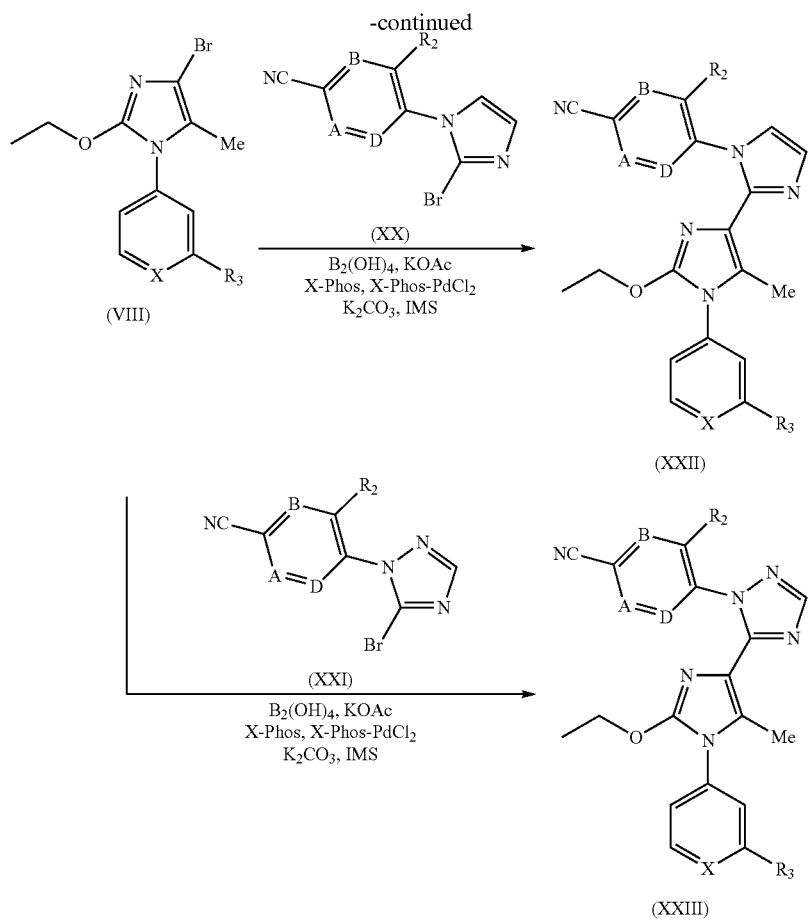

Compounds of formulae (II), (XXII), and (XXIII) may be obtained from compounds of formula (VIII) by reacting with compounds of formulae (IXX), (XX, and (XXI), respectively, in the presence of tetrahydroxydiboron, potassium acetate, potassium carbonate and a suitable catalyst, for example (2-dicyclohexylphosphino-2',4',6'-triisopropyl-1,1'-biphenyl)palladium(II) dichloride (X-Phos-Pd—Cl$_2$) with 2-dicyclohexylphosphino-2',4',6'-triisopropylbiphenyl (X-Phos), in a suitable solvent such as IMS at a suitable temperature between ambient and the boiling point of the solvent.

These compounds of formulae (II), (XXII), and (XXIII) can be manipulated further to compounds of formula (I) using analogous procedures to those shown in scheme A.

Other features of the invention will become apparent in the course of the following descriptions of exemplary embodiments which are given for illustration of the invention and are not intended to be limiting thereof

EXAMPLES

General Experimental Details

Reactions were not carried out under an inert atmosphere unless specified and all solvents and commercial reagents were used as received.

Purification by chromatography refers to purification using the CombiFlash® Companion purification system or the Biotage SP1 purification system. Where products were purified using an Isolute® SPE Si II cartridge, 'Isolute SPE Si cartridge' refers to a pre-packed polypropylene column containing unbonded activated silica with irregular particles with average size of 50 µm and nominal 60 Å porosity. Fractions containing the required product (identified by TLC and/or LCMS analysis) were pooled and concentrated in vacuo. Where HPLC was used for purification (Purification by MDAP) fractions containing the required product (identified by TLC and/or LCMS analysis) were pooled, the bulk of the organic fraction removed by evaporation, and the remaining aqueous fraction lyophilized, to give the final product. Alternatively the pooled product fraction was evaporated to dryness under reduced pressure. Where thin layer chromatography (TLC) has been used, it refers to silica gel TLC using plates, typically 3×6 cm silica gel on aluminium foil plates with a fluorescent indicator (254 nm), (e.g. Fluka 60778). Microwave experiments were carried out using a Biotage Initiator 60™ which uses a single-mode resonator and dynamic field tuning. Temperature from 40-250° C. can be achieved, and pressures of up to 30 bar can be reached.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane.

Compound names were generated using ACD/Name 2012.
Analytical LC-MS Conditions.
LC-MS Method 1.

The Waters ZQ quadrupole mass spectrometer with a C18-reverse-phase column (30×4.6 mm Phenomenex Luna 3 μm particle size), elution with A: water+0.1% formic acid; B: MeCN+0.1% formic acid. Gradient:

| Gradient - Time | flow (mL/min) | % A | % B |
|---|---|---|---|
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, UV (200 μl/min split to the ESI source with in-line HP 1100 PDA detector)

MS ionization method—Electrospray (positive and negative ion)

LC-MS Method 2.

Waters Micromass ZMD quadrupole mass spectrometer with a C18-reverse-phase column (30×4.6 mm Phenomenex Luna 3 μm particle size), elution with A: water+0.1% formic acid; B: MeCN+0.1% formic acid. Gradient:

| Gradient - Time | flow(mL/min) | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 μl split to MS with in-line UV detector)

MS ionization method—Electrospray (positive and negative ion)

LC-MS Method 3.

Waters Micromass ZQ2000 mass spectrometer with a C18-reverse-phase column (100×2.1 mm Acquity BEH with 1.7 μm particle size) maintained at 40° C., elution with A: water+0.1% formic acid; B: MeCN+0.1% formic acid. Alternatively, where specified, a C18-reverse-phase (100×2.1 mm Acquity UPLC BEH Shield 1.7 μm particle size) column was used.
Gradient:

| Gradient - Time | flow (mL/min) | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA

MS ionization method—Electrospray (positive/negative ion).

LC-MS Method 4.

Waters Platform LC quadrupole mass spectrometer with a C18-reverse-phase column (30×4.6 mm Phenomenex Luna 3 μm particle size), elution with A: water+0.1% formic acid; B: MeCN+0.1% formic acid. Gradient:

| Gradient - Time | flow (mL/min) | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, UV (Split—200 μl/min split to the ESI source with in-line HP 1100 DAD detection)

MS ionization method—Electrospray (positive and negative ion).

LC-MS Method 5.

Waters VG Platform II quadrupole spectrometer with a C18-reverse-phase column (30×4.6 mm Luna 3 μm particle size), elution with A: water+0.1% formic acid; B: MeCN+0.1% formic acid.
Gradient:

| Gradient - Time | flow | % A | % B |
|---|---|---|---|
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, UV (Split—200 μl/min split to the ESI source with in-line HP1050 DAD detection)

MS ionization method—Electrospray (positive and negative ion)

LC-MS Method U2.

Acquity H-Class (quaternary pump/PDA detector) plus QDa Mass Spectrometer with an Acquity UPLC BEH C18-reverse-phase column (1.7 μm particle size, 50×2.1 mm at 40° C.), elution with A: water+0.1% formic acid; B: MeCN+0.1% formic acid. Gradient:

| Gradient - Time | flow (mL/min) | % A | % B |
|---|---|---|---|
| 0.00 | 1.0 | 97 | 3 |
| 1.50 | 1.0 | 1 | 99 |
| 1.90 | 1.0 | 1 | 99 |
| 2.00 | 1.0 | 97 | 3 |
| 2.50 | 1.0 | 97 | 3 |

Detection—MS, UV

MS ionization method—Electrospray (positive and negative ion).

MDAP System:
Instrumentation: Agilent 1260 infinity purifications system.
Agilent 6100 series single Quadrupole LC/MS
Column: XSELECT CSH Prep C18 5 μm OBD, 30X150 mm, RT
Mobile Phase A: 0.1% aqueous formic acid
Mobile Phase B: 0.1% formic acid in acetonitrile
Flow: 60 ml/min
Gradient Program: 10%-95%, 22 min, centred around a specific focused gradient
Sample Injection of a 20-60 mg/ml solution in DMSO (+optional formic acid and water).

Abbreviations used in the experimental section:
AIBN Azobisisobutyronitrile
DCM Dichloromethane
DIPEA Di-isopropylethylamine
DMF N,N-dimethylformamide
DMSO Dimethylsulphoxide
$Et_2O$ Diethyl ether EtOAc Ethyl acetate
h Hour
HPLC High performance liquid chromatography
IMS Industrial methylated spirits
LC-MS Liquid chromatography-mass spectrometry
MeCN Acetonitrile
MDAP Mass Directed Automatic Purification
Min Minutes
NBS N-Bromosuccinimide
Rt Retention time
RT Room temperature
THF Tetrahydrofuran In the procedures that follow, some of the starting materials are identified through an "Intermediate" or "Example" number. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

The present invention will now be further described by the following examples.

Example 1

4-(5-{5-Methyl-2-oxo-1-[3-(trifluoromethyl)phenyl]-2,3-dihydro-1H-imidazol-4-yl}-1H-pyrazol-1-yl)benzonitrile

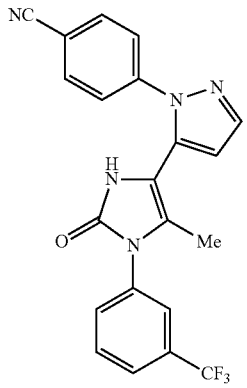 [SMILES: Cc1c(-c2ccnn2-c2ccc(C#N)cc2)[nH]c(=O)n1-c1cccc(C(F)(F)F)c1]

Intermediate 1

1-Prop-2-yn-1-yl-3-[3-(trifluoromethyl)phenyl]urea

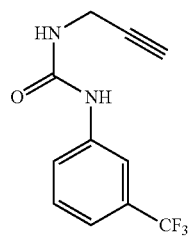 [SMILES: C#CCNC(=O)Nc1cccc(C(F)(F)F)c1]

A solution of propargyl amine (4.41 g, 5.13 mL, 80 mmol) in MeCN (30 mL) was added to a stirred solution of 3-(trifluoromethyl)phenyl isocyanate (15.0 g, 12.12 mL, 80 mmol) in MeCN (60 mL) under a nitrogen atmosphere. The reaction mixture was cooled with a RT cooling bath and the rate of addition was such that the internal temperature did not exceed 35° C. After 1.5 h the mixture was concentrated in vacuo. EtOAc (10 ml) was added to the residue and the mixture was sonicated for 2 minutes. The resultant slurry was diluted with cyclohexane (40 ml). The mixture was stirred for 10 minutes and the solid was then recovered by filtration. The mother liquors were concentrated in vacuo and the residue dissolved in EtOAc (10 mL). Dilution with cyclohexane (90 ml) precipitated a second batch of product which was recovered by filtration. The two batches were combined as an ethyl acetate solution and concentrated in vacuo to afford the title compound as a fawn solid (16.65 g).

LCMS (Method 2): Rt=3.22 min, m/z 243 [M+H]$^+$

Intermediate 2

5-Methyl-1-[3-(trifluoromethyl)phenyl]-1,3-dihydro-2H-imidazol-2-one

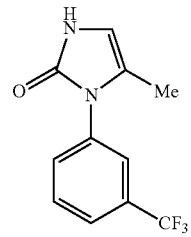 [SMILES: Cc1c[nH]c(=O)n1-c1cccc(C(F)(F)F)c1]

A solution of 1-prop-2-yn-1-yl-3-[3-(trifluoromethyl)phenyl]urea (intermediate 1) (11.2 g, 46 mmol) in THF (60 mL) and acetonitrile (120 mL) was added, under a nitrogen atmosphere, to a stirred suspension of sodium hydride (60% dispersion in mineral oil) (4.62 g, 115 mmol) in THF (60 mL) at such a rate that gas evolution was not over-vigorous and the internal temperature remained below 30° C. The mixture was stirred at RT for 2.5 h, a thick precipitate having formed within 1 h. The reaction mixture was cautiously quenched with water (15 mL) and the resulting solution was treated with 1 M hydrochloric acid (150 mL, 150 mmol). The mixture was stirred for 4 hours then allowed to stand for 15 hours. Saturated brine (150 mL) was added and the phases were partitioned. The aqueous phase was extracted with EtOAc (100 mL). The combined organic phase was washed with saturated brine (100 mL), dried (sodium sulfate) and concentrated in vacuo. The residue was triturated with EtOAc (33 mL). The resultant solid was taken into DCM and filtered. The filtrate was concentrated in vacuo to afford the title compound (10.0 g) as a fawn solid.

LCMS (Method 1): Rt=2.63 min, m/z 243 [M+H]$^+$

Intermediate 3

2-Ethoxy-5-methyl-1-[3-(trifluoromethyl)phenyl]-1H-imidazole

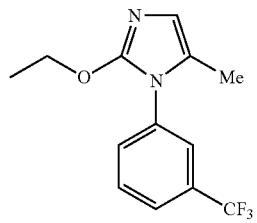 [SMILES: CCOc1ncc(C)n1-c1cccc(C(F)(F)F)c1]

A solution of triethyloxonium tetrafluoroborate (9.0 g, 47 mmol) in DCM (62 mL) was added to a stirred solution of 5-methyl-1-[3-(trifluoromethyl)phenyl]-1,3-dihydro-2H-imidazol-2-one (9.0 g, 37 mmol) in DCM (124 mL) under a nitrogen atmosphere. The solution was stirred at RT for 2.5 h then treated with water (50 mL) then 1 M sodium hydroxide (50 mL). The phases were partitioned. The aqueous phase was washed with DCM (2×50 mL). The combined organic phase was dried (sodium sulfate). The solution of the crude product was filtered through 2×50 g flash SCX 2 cartridges. Each cartridge was rinsed with 10% methanol in DCM (100 mL) then the product fraction was eluted with 2M methanolic ammonia solution (100 mL). The fractions recovered with methanolic ammonia were combined and concentrated in vacuo to afford the title compound (7.92 g) as a brown solid.

LCMS (Method 1): Rt=2.41 min, m/z 271 [M+H]$^+$

Intermediate 4

4-Bromo-2-ethoxy-5-methyl-1-[3-(trifluoromethyl)phenyl]-1H-imidazole

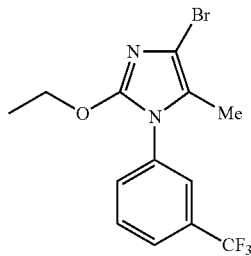 [SMILES: CCOc1nc(Br)c(C)n1-c1cccc(C(F)(F)F)c1]

A solution of NBS (5.16 g, 29 mmol) in MeCN (60 mL) was added to a stirred solution of 2-ethoxy-5-methyl-1-[3-(trifluoromethyl)phenyl]-1H-imidazole (7.92 g, 29 mmol) in MeCN (115 mL) at such a rate that the internal temperature of the mixture did not exceed 25° C. (a RT cooling bath was used). After 0.5 h the mixture was diluted with water (50 mL) and saturated sodium carbonate (aq) (50 mL). Ethyl acetate (50 mL) was added. The mixture was stirred vigorously then the phases were separated. The organic phase was washed with saturated brine (50 mL), dried (sodium sulfate) and concentrated in vacuo. The residue was taken into dichloromethane and filtered through a 25 g Si II SPE cartridge. The cartridge was washed with DCM and 10% EtOAc in DCM.

The filtrate was concentrated in vacuo to afford the title compound as an off-white solid (8.93 g).

LCMS (Method 1): Rt=3.86 min, m/z 349 [M($^{79}$Br)

Intermediate 5

4-(5-{2-Ethoxy-5-methyl-1-[3-(trifluoromethyl)phenyl]-1H-imidazol-4-yl}-1H-pyrazol-1-yl)benzonitrile

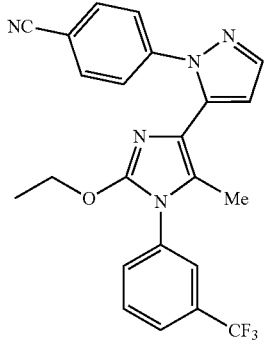 [SMILES: CCOc1nc(-c2ccnn2-c2ccc(C#N)cc2)c(C)n1-c1cccc(C(F)(F)F)c1]

A solution of 4-bromo-2-ethoxy-5-methyl-1-[3-(trifluoromethyl)phenyl]-1H-imidazole (3.14 g, 9 mmol) and 4-(5-tributylstannyl-pyrazol-1-yl)-benzonitrile (see WO2014009425A1, which is incorporated herein by reference in its entierty) (6.19 g, 13.5 mmol) in 1,4-dioxane (45 mL) was degassed by bubbling argon through the solution for 5 minutes. Tetrakis(triphenylphosphine)palladium(O) (0.52 g, 0.45 mmol) was added and after a further period of degassing the mixture was heated at 94° C. under an argon atmosphere during 17 h. The mixture was cooled to RT and filtered through a 50 g flash SCX 2 cartridge. The cartridge was eluted with DCM, 10% methanol in DCM then a 1:1 mixture of 2M ammonia in methanol and DCM. Concentration of the appropriate fractions in vacuo afforded the crude product. This was triturated with cyclohexane and dried in vacuo to afford the title compound (3.01 g).

LCMS (Method 1): Rt=3.84 min, m/z 438 [M+H]$^+$ 4-(5-{5-Methyl-2-oxo-1-[3-(trifluoromethyl)phenyl]-2,3-dihydro-1H-imidazol-4-yl}-1H-pyrazol-1-yl)benzonitrile Example 1

A suspension of 4-(5-{2-ethoxy-5-methyl-1-[3-(trifluoromethyl)phenyl]-1H-imidazol-4-yl}-1H-pyrazol-1-yl)benzonitrile (0.71 g, 1.6 mmol) in acetone (10 mL) and 1M hydrochloric acid (1.6 mL) was heated at 60° C. for 14 h. The mixture was cooled, diluted with acetone (50 mL) and filtered through a 5 g flash NH2 column. The filtrate was concentrated in vacuo. The residue was twice taken into acetonitrile and reconcentrated. The residue was triturated with acetone (10 mL) and dried in vacuo to afford the title compound (0.45 g)

LCMS (Method 3): Rt=4.32 min, m/z 410.1 [M+H]$^+$ $^1$H NMR (400 MHz, CDCl$_3$): δ 9.27 (1H, br s), 7.78 (1H, d J=1.8 Hz), 7.73-7.63 (4H, m), 7.60-7.56 (3H, m), 7.49 (1H, dJ=7.5 Hz), 6.56 (1H, d J=1.8 Hz), 1.84 (3H, S)

Example 2

4-(5-{5-Methyl-3-[3-(methylsulfonyl)propyl]-2-oxo-1-[3-(trifluoromethyl)phenyl]-2,3-dihydro-1H-imidazol-4-yl}-1H-pyrazol-1-yl)benzonitrile

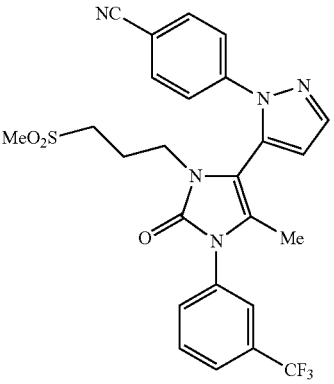 [SMILES: Cc1c(-c2ccnn2-c2ccc(C#N)cc2)n(CCCS(C)(=O)=O)c(=O)n1-c1cccc(C(F)(F)F)c1]

A mixture of 4-(5-{2-ethoxy-5-methyl-1-[3-(trifluoromethyl)phenyl]-1H-imidazol-4-yl}-1H-pyrazol-1-yl)benzonitrile (intermediate 5) (66 mg, 0.15 mmol) and 1-bromo-3-methanesulfonyl propane (201 mg, 1.0 mmol) in acetonitrile (0.20 mL) was heated at 120° C. for 6 h. The mix was cooled to RT and diluted with acetonitrile (2 mL) and water (1 mL) then treated with 1M sodium hydroxide (0.20 ml). The mixture was heated at 50° C. for 2 h. The cold mixture was diluted with water (10 mL) and extracted with EtOAc (2×10 mL). The combined organic phase was dried (sodium sulfate) and concentrated in vacuo. The residue was purified by MDAP to afford the title compound (10 mg).

LCMS (Method 3): Rt=4.38 min, m/z 530.1 [M+H]⁺

¹H NMR (400 MHz, CDCl₃): δ 7.89 (1H, d J=1.8 Hz), 7.74 (2H, d J=8.8 Hz), 7.71-7.57 (5H, m), 7.51 (1H, d J=7.7 Hz), 6.69 (1H, d J=1.8 Hz), 3.86-3.74 (1H, m), 3.42-3.32 (1H, m), 3.04 (2H, t J=8.0 Hz), 2.87 (3H, s), 2.10-1.96 (2H, m), 1.75 (3H, s)

Example 3

4-(5-{3,5-Dimethyl-2-oxo-1-[3-(trifluoromethyl)phenyl]-2,3-dihydro-1H-imidazol-4-yl}-1H-pyrazol-1-yl)benzonitrile

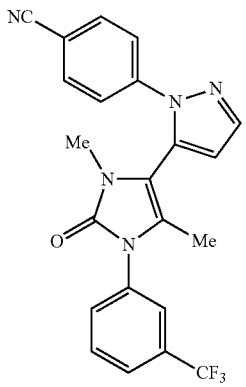 [SMILES: Cc1c(-c2ccnn2-c2ccc(C#N)cc2)n(C)c(=O)n1-c1cccc(C(F)(F)F)c1]

Sodium hydride (10 mg of a 60% dispersion in mineral oil, 0.25 mmol) was added to a stirred suspension of 4-(5-{5-methyl-2-oxo-1-[3-(trifluoromethyl)phenyl]-2,3-dihydro-1H-imidazol-4-yl}-1H-pyrazol-1-yl)benzonitrile (Example 1) (70 mg, 0.17 mmol) in THF (2.0 mL) under a nitrogen atmosphere. This resulted in degassing and the formation of a yellow solution. Iodomethane (0.031 mL, 0.5 mmol) was added and the mixture was stirred for 3 h. Water (10 mL) was added and the mixture was extracted with DCM (2×10 mL). The combined organic phase was dried (sodium sulfate) and concentrated in vacuo. The residue was purified by flash column chromatography (2 g Si II SPE eluted with 0-50% EtOAc in DCM in 10% increments). Concentration of the appropriate fractions in vacuo gave the title compound which was freeze-dried from acetonitrile/water to afford a fluffy white solid (50 mg).

LCMS (Method 3): Rt=4.57 min, m/z 424.1 [M+H]⁺

¹H NMR (400 MHz, CDCl₃): δ7.87 (1H, d J=1.8 Hz), 7.74 (2H, d J=8.7 Hz), 7.69-7.57 (5 Hz, m), 7.51 (1H, d J=7.7 Hz), 6.62 (1H, d J=1.8 Hz), 2.98 (3H, s), 1.76 (3H, s)

Example 4

Ethyl-5-[1-(4-cyanophenyl)-1H-pyrazol-5-yl]-4-methyl-2-oxo-3-[3-(trifluoromethyl)phenyl]-2,3-dihydro-1H-imidazole-1-carboxylate

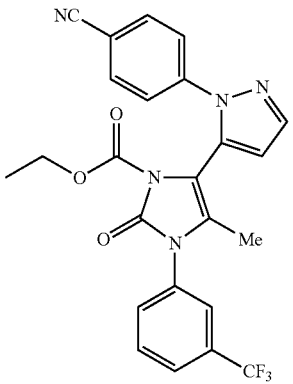

Sodium hydride (38 mg of a 60% dispersion in mineral oil, 0.95 mmol) was added to a solution of 4-(5-{5-methyl-2-oxo-1-[3-(trifluoromethyl)phenyl]-2,3-dihydro-1H-imidazol-4-yl}-1H-pyrazol-1-yl)benzonitrile (Example 1) (300 mg, 0.73 mmol) in DMF under a nitrogen atmosphere. The mixture was stirred for 5 minutes and the resultant yellow solution was treated with ethyl chloroformate (104 mg, 0.091 mL, 0.95 mmol). The mixture was stirred for 1 h then treated with water and extracted with EtOAc. The organic phase was washed with water and brine then dried (sodium sulfate) and concentrated in vacuo. The residue was purified by chromatography using silica gel eluting with 25%-50% ethyl acetate in cyclohexane. The product thus obtained was freeze-dried from acetonitrile-water to afford the title compound (194 mg) a white solid.

LCMS (Method 3): Rt=4.83 min, m/z 482.1 [M+H]⁺

¹H NMR (400 MHz, CDCl₃): δ 7.82 (1H, d J=1.7 Hz), 7.76-7.60 (7H, m), 7.52 (1H, d J=7.9 Hz), 6.56 (1H, d J=1.7 Hz), 4.17-4.07 (2H, m), 1.84 (3H, s), 1.12 (3H, t J=7.1 Hz)

Example 5

4-(5-{3-Acetyl-5-methyl-2-oxo-1-[3-(trifluoromethyl)phenyl]-2,3-dihydro-1H-imidazol-4-yl}-1H-pyrazol-1-yl)benzonitrile

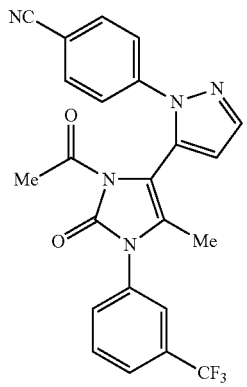 [SMILES: CC(=O)n1c(-c2ccnn2-c2ccc(C#N)cc2)c(C)n(-c2cccc(C(F)(F)F)c2)c1=O]

Sodium hydride (12.5 mg of a 60% dispersion in mineral oil, 0.31 mmol) was added to a stirred suspension of 4-(5-{5-methyl-2-oxo-1-[3-(trifluoromethyl)phenyl]-2,3-dihydro-1H-imidazol-4-yl}-1H-pyrazol-1-yl)benzonitrile (Example 1) (102 mg, 0.25 mmol) in THF (5.0 mL) under a nitrogen atmosphere. This resulted in degassing and the formation of a yellow solution. Acetyl chloride (0.022 mL, 0.5 mmol) was added and the mixture was stirred for 1 h then left to stand for 16 h. Water (10 mL) was added and the mixture was extracted with EtOAc (2×10 mL). The combined organic phase was dried (sodium sulfate) and concentrated in vacuo. The residue was purified by flash column chromatography (2 g Si II SPE eluted with DCM then 10% EtOAc in DCM). Concentration of the appropriate fractions in vacua gave the title compound which was freeze-dried from acetonitrile/water to afford a fluffy white solid (56 mg).

LCMS (Method 3): Rt=4.86 min, m/z 452.0 [M+1]$^+$ $^1$H NMR (400 MHz, CDCl$_3$) δ 7.80 (1H, d J=1.7 Hz), 7.77-7.66 (4H, m), 7.63-7.51 (4H, m), 6.51 (1H, d J=1.7 Hz), 2.44 (3H, s), 1.88 (3H, s)

Example 6

5-[1-(4-Cyanophenyl)-1H-pyrazol-5-yl]-N-ethyl-4-methyl-2-oxo-3-[3-(trifluoromethyl)phenyl]-2,3-dihydro-1H-imidazole-1-carboxamide

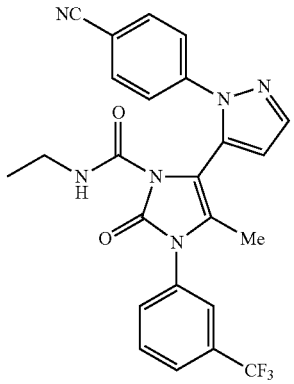 [SMILES: CCNC(=O)n1c(-c2ccnn2-c2ccc(C#N)cc2)c(C)n(-c2cccc(C(F)(F)F)c2)c1=O]

4-Nitrophenyl chloroformate (226 mg, 1.12 mmol) was added portion wise to a solution of 4-(5-{5-methyl-2-oxo-1-[3-(trifluoromethyl)phenyl]-2,3-dihydro-1H-imidazol-4-yl}-1H-pyrazol-1-yl)benzonitrile (Example 1) (409 mg, 1.0 mmol) and triethylamine (0.355 mL, 2.55 mmol) in DCM (12 mL) under a nitrogen atmosphere. The mixture was stirred for 2.75 h giving a yellow solution. A solution of ethylamine (3.0 mL of a 2M solution in THF, 6 mmol) was added. The mixture was stirred for a further 2.5 h then concentrated in vacuo. The residue was chromatographed on silica gel eluting with 10-40% EtOAc in DCM then recolumned on silica gel with 25-60% EtOAc in cyclohexane to afford the title compound as a colourless foam after drying in vacuo.

LCMS (Method 3): Rt=4.95 min, m/z 481.1 [M+H]$^+$ $^1$H NMR (400 MHz, CDCl$_3$): δ 8.38 (1H, t J=5.3 Hz), 7.81 (1H, d J=1.8 Hz), 7.77-7.66 (4H, m), 7.63-7.58 (3H, m), 7.53 (1H, d J=7.9 Hz), 6.56 (1H, d J=1.8 Hz), 3.21-3.13 (2H, m), 1.87 (3H, s), 1.04 (3H, t J=7.2 Hz).

In Table 1, Method A refers to compounds prepared in an analogous manner to Example 4, Method B refers to compounds prepared in analogous manner to Example 5, Method C refers to compounds prepared in analogous manner to Example 6, and Method D refers to compounds prepared in an analogous manner to Example 3 (where salts of amines were used in place of the free base additional triethylamine was added to the reaction mixture to allow for this). In the table below, where rotameric signals have been identified in the NMR spectrum, these have been labelled by *.

TABLE 1

| Ex | Structure | Method | 1H NMR | LC-MS Method 3 |
|---|---|---|---|---|
| 7 | 5-[1-(4-Cyanophenyl)-1H-pyrazol-5-yl]-N-(2-hydroxyethyl)-4-methyl-2-oxo-3-[3-(trifluoromethyl)phenyl]-2,3-dihydro-1H-imidazole-1-carboxamide | C | $^1$H NMR (400 MHz, CDCl$_3$): δ 8.74, (1H, t J = 5.5 Hz), 7.81 (1H,d J = 1.8 Hz), 7.78-7.58 (7H, m), 7.53 (1H, d J = 7.9 Hz), 6.56 (1H, d J = 1.8 Hz), 3.61 (2H, q J = 5.4 Hz), 3.33 (2H, 1, J = 5.4 Hz), 1.88 (3H, s), 1.79 (1H, t J = 5.3 Hz) | Rt = 4.36 min, m/z = 497.1 [M + H]$^+$ |

TABLE 1-continued

| Ex | Structure | Method | 1H NMR | LC-MS Method 3 |
|---|---|---|---|---|
| 8 | 5-[1-(4-Cyanophenyl)-1H-pyrazol-5-yl]-N-(3-hydroxypropyl)-4-methyl-2-oxo-3-[3-(trifluoromethyl)phenyl]-2,3-dihydro-1H-imidazole-1-carboxamide | C | $^1$H NMR (400 MHz, DMSO): δ 8.36 (1H, t J = 5.7 Hz), 8.01 (1H, s), 7.94-7.78 (6H, m), 7.66 (2H, d J = 8.7 Hz), 6.63 (1H, d J = 1.8 Hz), 4.41 (1H, t J = 4.9 Hz), 3.36-3.20 (2H, m, partially obscured by water peak), 3.0 (2H, q J = 6.3Hz), (1.88, 3H, s), 1.41-1.23 (2H, m) | Rt = 4.42 min, m/z = 511.1 [M + H]$^+$ |
| 9 | 5-[1-(4-Cyanophenyl)-1H-pyrazol-5-yl]-N-[3-(dimethylamino)propyl]-4-methyl-2-oxo-3-[3-(trifluoromethyl)phenyl]-2,3-dihydro-1H-imidazole-1-carboxamide | C | $^1$H NMR (400 MHz, CDCl$_3$): δ 8.57 (1H, br s), 7.81 (1H, d J = 1.7 Hz), 7.77-7.66 (4H, m), 7.63-7.59 (3H, m), 7.75 (1H, d J = 7.5 Hz), 6.55 (1H, d J = 1.7 Hz), 3.24-3.16 (2H, m), 2.34 (2H, t J = 7.3 Hz), 2.26 (6H, s), 1.87 (3H s), 1.66-1.58 (2H, m) | Rt = 3.51 min, m/z = 538.2 [M + H]$^+$ |
| 10 | 4-(5-{3-Butanoyl-5-methyl-2-oxo-1-[3-(trifluoromethyl)phenyl]-2,3-dihydro-1H-imidazol-4-yl}-1H-pyrazol-1-yl)benzonitrile | B | $^1$H NMR (400 MHz, CDCl$_3$): δ 7.80 (1H, d J = 1.8 Hz), 7.76-7.51 (8H, m), 6.51 (1H, d J = 1.8 Hz), 2.89 (1H, d J = 17.4 Hz of t J = 7.2 Hz), 2.75 (1H, d J = 17.4 Hz of t J = 7.4 Hz), 1.90 (3H, s), 1.49-1.39 (2H, m), 0.79 (3H, t J = 7.4 Hz) | Rt = 5.28 min, m/z = 480.1 [M + H]$^+$ |

TABLE 1-continued

| Ex | Structure | Method | 1H NMR | LC-MS Method 3 |
|---|---|---|---|---|
| 11 | 5-[1-(4-Cyanophenyl)-1H-pyrazol-5-yl]-N-(2-methoxyethyl)-4-methyl-2-oxo-3-[3-(trifluoromethyl)phenyl]-2,3-dihydro-1H-imidazole-1-carboxamide | C | $^{1}$H NMR (400 MHz, CDCl$_3$): δ 8.65 (1H, s), 7.81 (1H, d J = 1.6 Hz), 7.77-7.59 (7H, m), 7.53 (1H, d J = 7.8 Hz), 6.55 (1H, d J = 1.6 Hz), 3.42-3.29 (7H, m), 1.85 (3H, s) | Rt = 4.84 min, m/z = 511.1 [M + H]$^+$ |
| 12 | 5-[1-(4-Cyanophenyl)-1H-pyrazol-5-yl]-N-[2-(dimethylamino)ethyl]-4-methyl-2-oxo-3-[3-(trifluoromethyl)phenyl]-2,3-dihydro-1H-imidazole-1-carboxamide | C | $^{1}$H NMR (400 MHz, CDCl$_3$): δ 8.60 (1H, t J = 4.9 Hz), 7.81 (1H, d J = 1.8 Hz), 7.76-7.59 (7H, m), 7.52 (1H, d J = 7.9 Hz), 6.55 (1H, d J = 1.8 Hz), 3.23 (2H, q J = 5.8 Hz), 2.32 (2H, t J = 6.2 Hz), 2.18 (6H, s), 1.84 (3H, s) | Rt = 3.47 min, m/z = 524.1 [M + H]$^+$ |
| 13 | 5-[1-(4-Cyanophenyl)-1H-pyrazol-5-yl]-4-methyl-N-[2-(methylsulfonyl)ethyl]-2-oxo-3-[3-(trifluoromethyl)phenyl]-2,3-dihydro-1H-imidazole-1-carboxamide | C | $^{1}$H NMR (400 MHz, CDCl$_3$): δ 8.99 (1H, t J = 5.8 Hz), 7.83 (1H, d J = 1.8 Hz), 7.77-7.65 (4H, m), 7.63-7.59 (3H, m), 7.53 (1H, d J = 830 Hz), 6.56 (1H, d J = 1.8 Hz), 3.76-3.62 (2H, m), 3.10 (2H, t J = 6.2 Hz), 2.90 (3H, s), 1.85 (3H, s) | Rt = 4.52 min, m/z = 559.0 [M + H]$^+$ |

TABLE 1-continued

| Ex | Structure | Method | 1H NMR | LC-MS Method 3 |
|---|---|---|---|---|
| 14 | 5-[1-(4-Cyanophenyl)-1H-pyrazol-5-yl]-4-methyl-2-oxo-N-(tetrahydrofuran-3-yl)-3-[3-(trifluoromethyl)phenyl]-2,3-dihydro-1H-imidazole-1-carboxamide | C | $^1$H NMR (400 MHz, CDCl$_3$): δ 8.65 (1H, t J = 6.0 Hz), 7.82 (1H, d J = 1.8 Hz), 7.78-7.66 (4H, m), 7.63-7.57 (3H, m), 7.53 (1H, d J = 7.6 Hz), 6.57-6.55 (1H, m), 4.26-4.16 (1H, m), 3.89-3.72 (3H, m), 3.63 (0.5H*, m), 3.40 (0.5 H*, m), 2.22-2.07 (1H, m), 1.89 (3H, s), 1.81-1.72 (0.5H*, m), 1.64-1.56 (0.5H*, m) | Rt = 436 min, m/z = 523.1 [M + H]$^+$ |
| 15 | 5-[1-(4-Cyanophenyl)-1H-pyrazol-5-yl]-4-methyl-2-oxo-N-[(3S)-tetrahydrfuran-3-yl]-3-[3-(trifluoromethyl)phenyl]-2,3-dihydro-1H-imidazole-1-carboxamide | C | $^1$H NMR (400 MHz, CDCl$_3$): δ 8.65 (1H, t J = 6.0 Hz), 7.82 (1H, d J = 1.8 Hz), 7.78-7.66 (4H, m), 7.63-7.57 (3H, m), 7.53 (1H, d J = 7.6 Hz), 6.57-6.55 (1H, m), 4.26-4.16 (1H, m), 3.89-3.72 (3H, m), 3.63 (0.5H*, m), 3.40 (0.5 H*, m), 2.22-2.07 (1H, m), 1.89 (3H, s), 1.81-1.72 (0.5H*, m), 1.64-1.56 (0.5H8, m) | Rt = 4.76 min, m/z = 523.1 [M + H]$^+$ |
| 16 | 5-[1-(4-Cyanophenyl)-1H-pyrazol-5-yl]-4-methyl-2-oxo-N-[(3R)-tetrahydrofuran-3-yl]-3-[3-(trifluoromethyl)phenyl]-2,3-dihydro-1H-imidazole-1-carboxamide | C | $^1$H NMR (400 MHz, CDCl$_3$): δ 8.65 (1H, t J = 6.0 Hz), 7.82 (1H, d J = 1.8 Hz), 7.78-7.66 (4H, m), 7.63-7.57(3H, m), 7.53 (1H, d 4.26-4.16 (1H, m), 3.89-3.72 (3H, m), 3.63 (0.5H*, m), 3.40 (0.5 H*, m), 2.22-2.07 (1H, m), 1.89 (3H, s), 1.81-1.72 (0.5H*, m), 1.64-1.56 (0.5H*, m) | Rt = 4.72 min, m/z = 523.2 [M + H]$^+$ |

TABLE 1-continued

| Ex | Structure | Method | 1H NMR | LC-MS Method 3 |
|---|---|---|---|---|
| 17 | 5-[1-(4-Cyanophenyl)-1H-pyrazol-5-yl]-4-methyl-N-[(1-methyl-1H-pyrazol-3-yl)methyl]-2-oxo-3-[3-(trifluoromethyl)phenyl]-2,3-dihydro-1H-imidazole-1-carboxamide | C | ¹H NMR (400 MHz, CDCl₃): δ 8.83 (1H, t J = 5.2Hz), 7.81 (1H, d J = 1.7 Hz), 7.76-7.49 (8H, m), 7.25 (1H, d J = 2.2 Hz) 6.56 (1H, d J = 1.7 Hz), 5.91 (1H, d J = 2.2 Hz), 4.37 (1H, d J = 15.0 Hz of d J = 5.7 Hz), 4.27 (1H, d J = 15.0 Hz of d J = 4.9), 3.83 (3H, s), 1.87 (3H, s) | Rt = 4.69 min, m/z = 547.1 [M + H]⁺ |
| 18 | Methyl-5-[1-(4-cyanophenyl)-1H-pyrazol-5-yl]-4-methyl-2-oxo-3-[3-(trifluoromethyl)phenyl]-2,3-dihydro-1H-imidazole-1-carboxylate | A | ¹HNMR (400 MHz, CDCl₃): δ 7.82 (1H, d J = 1.8 Hz), 7.76-7.70 (3H, m), 7.69-7.59 (4H, m), 7.51 (1H, d J = 7.9 Hz), 6.57 (1H, d J = 1.8 Hz), 3.71 (3H, s), 1.84 (3H, s) | Rt = 4.63 min, m/z = 468.1 [M + H]⁺ |
| 19 | 4-(5-{5-Methyl-2-oxo-3-pentanoyl-1-[3-(trifluoromethyl)phenyl]-2,3-dihydro-1H-imidazol-4-yl}-1H-pyrazol-1-yl)benzonitrile | B | ¹H NMR (400 MHz, CDCl₃): δ 7.80 (1H, d J = 1.7 Hz), 7.76-7.65 (4H, m), 7.64-7.51 (4H, m), 6.50 (1H, d J = 1.7 Hz), 2.95-2.74 (2H, m), 1.90 (3H, s), 1.42-1.32 (2H, m), 1.22-1.12 (2H, m), 0.83 (3H, t J = 7.4 Hz) | Rt = 5.46 min, m/z = 4.94.1 [M + H]⁺ |

| Ex | Structure | Method | 1H NMR | LC-MS Method 3 |
|---|---|---|---|---|
| 20 | 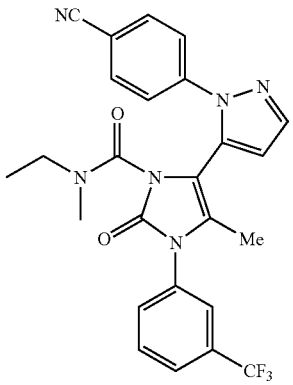<br>tert-Butyl-{5-[1-(4-cyanophenyl)-1H-pyrazol-5-yl]-4-methyl-2-oxo-3-[3-(trifluoromethyl)phenyl]-2,3-dihydro-1H-imidazol-1-yl}acetate | D | $^1$H NMR (400 MHz, CDCl$_3$): δ 7.84 (1H, d J = 1.8 Hz) 7.81-7.73 (4H, m), 7.68-7.58 (2H, m), 7.55 (1H, s), 7.44 (1H, d J = 7.8 Hz), 7.57 (1H, d J = 1.8 Hz), 4.40-4.20 (2H, m), 1.48 (3H, s), 1.37 (9H, s) | Rt = 5.23 min, m/z = 524.2 [M + Na]$^+$ |

Example 21

5-[1-(4-Cyanophenyl)-1H-pyrazol-5-yl]-N-ethyl-N,4-dimethyl-2-oxo-3-[3-(trifluoromethyl)phenyl]-2,3-dihydro-1H-imidazole-1-carboxamide

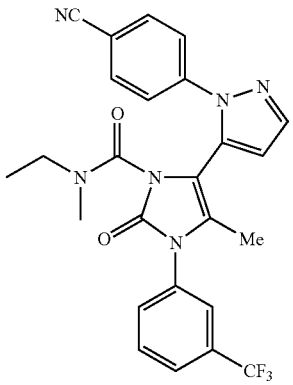 [SMILES: CCN(C)C(=O)n1c(-c2ccnn2-c2ccc(C#N)cc2)c(C)n(-c2cccc(C(F)(F)F)c2)c1=O]

4-(5-{5-Methyl-2-oxo-1-[3-(trifluoromethyl)phenyl]-2,3-dihydro-1H-imidazol-4-yl}-1H-pyrazol-1-yl)benzonitrile (Example 1) (107 mg, 0.262 mmol) was stirred in DCM (3 mL) and triethylamine (0.109 mL, 0.786 mmol) with N,N-dimethylaminopyridine (2 mg). To this mixture was added 4-nitrophenyl chloroformate (106 mg, 0.524 mmol) and the resulting mixture stirred at RT for 1 h. N-methylethylamine (93 mg, 1.57 mmol) in DCM (1 mL) was then added and stirring was continued for a further 2 h. The mixture was diluted with more DCM, washed with water, the organic phase separated, dried over Na$_2$SO$_4$ and evaporated. The product was purified by chromatography on a 12 g silica gel column, eluting with a gradient of 20% to 60% EtOAc in cyclohexane. The gum thus obtained was dissolved in a small quantity (<1 mL) of EtOAc and diluted with cyclohexane resulting in a formation of a white solid which was filtered off and dried. (65 mg, 50%).

LCMS (Method 3): R t=4.70 min, m/z 495.1 [M+H]$^+$ $^1$H NMR (400 MHz, DMSO at 80° C.): δ 7.93 (2H, d J=8.4 Hz), 7.83 (1H, d J=1.8 Hz), 7.81-7.72 (5H, m), 7.68-7.64 (1H, m), 6.62 (1H, d J=1.8 Hz), 3.24 (2H, q J=6.7 Hz), 2.80 (3H, s), 1.63 (3H, s), 1.0 (3H, t J=6.8 Hz).

Example 22

{5-[1-(4-Cyanophenyl)-1H-pyrazol-5-yl]-4-methyl-2-oxo-3-[3-(trifluoromethyl)phenyl]-2,3-dihydro-1H-imidazol-1-yl}acetic acid

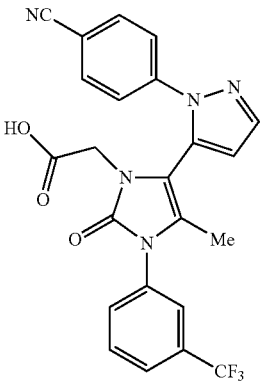 [SMILES: Cc1c(-c2ccnn2-c2ccc(C#N)cc2)n(CC(=O)O)c(=O)n1-c1cccc(C(F)(F)F)c1]

tert-Butyl-{5-[1-(4-cyanophenyl)-1H-pyrazol-5-yl]-4-methyl-2-oxo-3-[3-(trifluoromethyl)phenyl]-2,3-dihydro-1H-imidazol-1-yl}acetate (Example 20) (75 mg, 0.143 mmol) was stirred in DCM (3 mL) and water (0.03 mL). To this mixture was added TFA (0.1 mL) and the mixture stirred overnight. Reaction was incomplete so further TFA (0.5 mL) was added and after 1 h 30 minutes, a further 1 ml was added. After 4 h reaction was complete, solvents were evaporated and the residue partitioned between EtOAc and water. The organic phase was separated, dried over Na$_2$SO$_4$ and evaporated to give the title compound as a gum.

LCMS (Method 1): Rt 3.14 min., [M+H]$^+$ 468

$^1$H NMR (CDCl$_3$): δ 7.87 (1H, d J=1.8 Hz), 7.75-7.66 (5H, m), 7.61 (1H, t J=8.0 Hz), 7.55 (1H, s), 7.43 (1H, d J=8.0 Hz), 6.63 (1H, d J=1.8 Hz), 4.46-4.32 (2H, m), 1.50 (3H, s) one proton not observed.

Example 23

2-{5-[1-(4-Cyanophenyl)-1H-pyrazol-5-yl]-4-methyl-2-oxo-3-[3-(trifluoromethyl)phenyl]-2,3-dihydro-1H-imidazol-1-yl}-N-methylacetamide

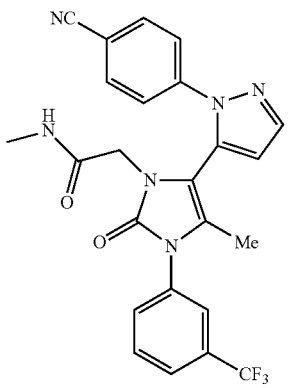 [SMILES: CNC(=O)Cn1c(-c2ccnn2-c2ccc(C#N)cc2)c(C)n(-c2cccc(C(F)(F)F)c2)c1=O]

1,1'-carbonyl diimidazole (45 mg, 0.278 mmol) was added to a solution of {5-[1-(4-cyanophenyl)-1H-pyrazol-5-yl]-4-methyl-2-oxo-3-[3-(trifluoromethyl)phenyl]-2,3-dihydro-1H-imidazol-1-yl}acetic acid (Example 22) (65 mg, 0.139 mmol) in THF (2.0 mL). The mixture was stirred for 1.25 h then a 2M methylamine in THF (0.278 mL, 0.556 mmol) was added. The mixture was stirred for 45 min then a second aliquot of 2M methylamine in THF (0.278 mL, 0.556 mmol) was added. The mixture was stirred for a further 40 minutes then partitioned between EtOAc and water. The phases were partitioned. The organic phase was dried over $Na_2SO_4$ and evaporated. The product was purified by chromatography on a 12 g silica gel column, eluting with 5% methanol in DCM. The material thus obtained was freeze dried from acetonitrile-water to afford the title compound (35 mg) a white solid.

LCMS (Method 3): Rt=4.10 min, m/z 481.1 [M+H]$^+$ $^1$H NMR (400 MHz, CDCl$_3$): δ 7.86 (1H, d J=1.8 Hz), 7.76-7.60 (6H, m) 7.56, (1H, s) 7.45 (1H, d J=7.7 Hz), 6.68 (1H, d J=1.8 Hz), 6.23 (1H, br s), 4.28-4.08 (2H, m), 2.75 (3H, d J=4.8 Hz), 1.56 (3H, s overlapping with water signal).

Example 24

Benzenesulfonate 3-[({5-[1-(4-cyanophenyl)-1H-pyrazol-5-yl]-4-methyl-2-oxo-3-[3-(trifluoromethyl)phenyl]-2,3-dihydro-1H-imidazol-1-yl}carbonyl)amino]-N,N,N-trimethylpropan-1-aminium

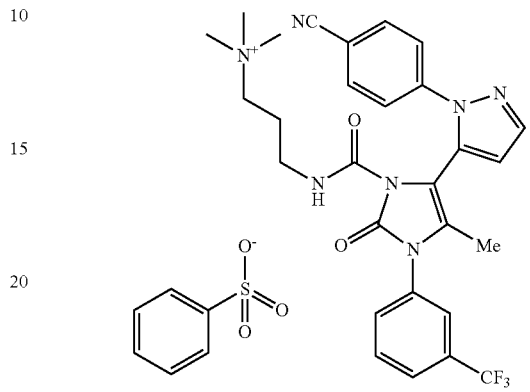

Methyl benzenesulfonate (0.019 mL, 0.14 mmol) was added to a solution of 5-[1-(4-cyanophenyl)-1H-pyrazol-5-yl]-N-[3-(dimethylamino)propyl]-4-methyl-2-oxo-3-[3-(trifluoromethyl)phenyl]-2,3-dihydro-1H-imidazole-1-carboxamide (Example 9) (77 mg, 0.14 mmol) in THF (3.0 mL). The mixture was stirred for 2 hr then allowed to stand at RT for 2 days. Water (15 mL) and EtOAc (15 ml) were added with stirring. The phases were separated. The aqueous phase was washed with EtOAc (15 mL) then diluted with MeCN. The solvents were removed by lyophilisation to afford the title compound (70 mg) a white solid.

LCMS (Method 3): Rt=3.52 min, m/z 552.2 [M]$^+$ $^1$H NMR (400 MHz, DMSO): δ 8.47 (1H, t J=6.0 Hz) 7.99-7.80 (7H, m), 7.69 (2H, d J=8.7 Hz) 7.61-7.58 (2H, m), 7.34-7.28 (3H, m), 6.64 (1H, d J=1.8 Hz) 3.15 (2H, t J=8.2 Hz), 3.04-2.97 (11H, m), 1.89 (3H, s), 1.73-1.63 (2H, m)

The following compound was prepared by analogous procedure to that used in Example 24.

TABLE 2

| Ex | Structure | $^1$H NMR | LC-MS Method 3 |
|---|---|---|---|
| 25 | Benzenesulfonate 2-[(({5-[1[(4-cyanophenyl)-1H-pyrazol-5-yl]-4-methyl-2-oxo-3-[3-(trifluoromethyl)phenyl]-2,3-dihydro-1H-imidazol-1-yl}carbonyl)amino]-N,N,N-trimethylethanaminium | $^1$H NMR (400 MHz, DMSO): δ 8.61 (1H, t J = 5.9 Hz) 8.02-7.82 (7H, m) 7.70 (2H, d J = 8.8 Hz), 7.61-7.57 (2H, m), 7.34-7.26 (3H, m), 6.65 (1H, d J = 1.7 Hz) 3.45-3.35 (2H, m), 3.22-3.10 (2H, m), 2.99 (9H, s) 1.90 (3H, s) | Rt =3.51 min, m/z = 538.1 [M]+ |

Example 26

4-(5-{3-Butyl-5-methyl-2-oxo-1-[3-(trifluoromethyl)phenyl]-2,3-dihydro-1H-imidazol-4-yl}-1H-pyrazol-1-yl)benzonitrile

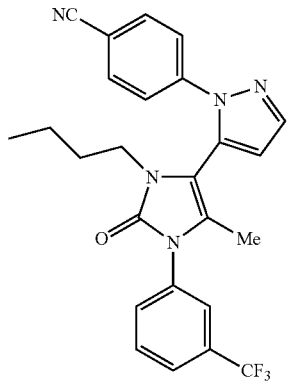 [SMILES: CCCCn1c(-c2ccnn2-c2ccc(C#N)cc2)c(C)n(-c2cccc(C(F)(F)F)c2)c1=O]

4-(5-{5-Methyl-2-oxo-1-[3-(trifluoromethyl)phenyl]-2,3-dihydro-1H-imidazol-4-yl}-1H-pyrazol-1-yl)benzonitrile (Example 1) (102 mg, 0.25 mmol) was added to a stirred mixture of potassium tert-butoxide (42 mg, 0.375 mmol) and THF (2.0 mL) under a nitrogen atmosphere. This resulted in the formation of a yellow solution. 1-Iodo-butane (0.057 mL, 0.5 mmol) was added and the mixture was stirred for 7 h then left to stand for 16 h. Water (10 mL) was added and the mixture was extracted with DCM (3×10 mL). The combined organic phase was dried (sodium sulfate) and concentrated in vacuo. The residue was purified by flash column chromatography (2 g Si II SPE eluted with DCM). The crude product thus obtained was further purified by flash column chromatography (2 g Si II SPE eluted with 20% EtOAc in cyclohexane). Concentration of the appropriate fractions in vacuo gave the title compound which was freeze-dried from acetonitrile/water to afford a white solid (25 mg).

LCMS (Method 3): Rt=5.24 min, m/z 466.1 [M+H]$^+$ $^1$H NMR (400 MHz, CDCl$_3$): $^1$H NMR (400 MHz, CDCl3) δ 7.87 (1H, d J=1.7 Hz), 7.73 (2H, d J=8.7 Hz), 7.67-7.57 (5H, m), 7.50 (1H, d J=7.5 Hz), 6.63 (1H d J=1.7 Hz), 3.61 (1H, m), 3.20 (1H, m) 1.72 (3H, s), 1.50-1.35 (2H, m), 1.27-1.15, (2H, m), 0.81 (3H, t J=7.4 Hz)

Example 27

4-(5-{5-Methyl-3-(methylsulfonyl)-2-oxo-1-[3-(trifluoromethyl)phenyl]-2,3-dihydro-1H-imidazol-4-yl}-1H-pyrazol-1-yl)benzonitrile

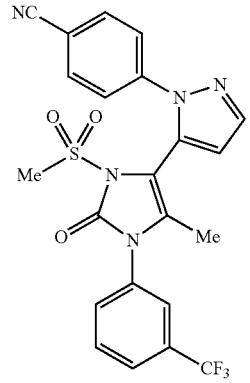 [SMILES: Cc1c(-c2ccnn2-c2ccc(C#N)cc2)n(S(C)(=O)=O)c(=O)n1-c1cccc(C(F)(F)F)c1]

Sodium hydride (12 mg of a 60% dispersion in mineral oil, 0.30 mmol) was added to a solution of 4-(5-{5-methyl-2-oxo-1-[3-(trifluoromethyl)phenyl]-2,3-dihydro-1H-imidazol-4-yl}-1H-pyrazol-1-yl)benzonitrile (Example 1) (94 mg, 0.23 mmol) in DMF (1.5 mL) under a nitrogen atmosphere. The mixture was stirred for 5 minutes and the resultant yellow solution was treated with methanesulfonyl chloride (32 mg, 21.4 μL, 0.28 mmol). The mixture was stirred for 2 h then treated with water and extracted with EtOAc. The organic phase was washed with water and brine then dried (sodium sulfate) and concentrated in vacuo. T he residue was purified by chromatography using silica gel eluting with 25%-60% ethyl acetate in cyclohexane. The product thus obtained was freeze-dried from acetonitrile-water to afford the title compound (54 mg) a white solid.

LCMS (Method 3): Rt=4.70 min, m/z=488.1 [M+H]$^+$ $^1$H NMR (400 MHz, CDCl$_3$): $^1$H NMR (400 MHz, CDCl3) δ 7.83 (1H, d J=1.8 Hz), 7.80-7.73 (3H, m), 7.69 (1H, t J=7.9 Hz), 7.66 (3H, m), 7.56 (1H, d J=8.0 Hz), 6.63 (1H, d J=1.8 Hz), 3.07 (3H, s), 1.92 (3H, s)

The following compounds were prepared by analogous procedure to that used in Example 26. In the table below, where rotameric signals have been identified in the NMR spectrum, these have been labelled by *.

TABLE 3

| Ex | Structure | $^1$H NMR | LC-MS Method 3 |
|---|---|---|---|
| 28 | 4-{5-[5-Methyl-3-(1-methyl-butyl)-2-oxo-1-(3-trifluoromethyl-phenyl)-2,3-dihydro-1H-imidazol-4-yl]pyrazol-1-yl}-benzonitrile | $^1$H NMR (400 MHz, d6-DMSO): δ 8.04-7.98 (3H, m), 7.85-7.66 (6H, m), 6.83-6.77 (1H*, m), 3.45-3.12 (1H*, m), 1.87-1.52 (4H*, m), 1.33-1.22 (1H, m), 1.08-0.79 (5H*, m), 0.69-0.65 (3H*, m) | Rt = 5.49 min, m/z = 480.1 [M + H]+ |

TABLE 3-continued

| Ex | Structure | ¹H NMR | LC-MS Method 3 |
|---|---|---|---|
| 29 | 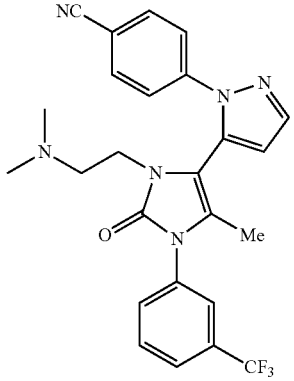 [SMILES: Cc1c(-c2ccnn2-c2ccc(C#N)cc2)n(CCN(C)C)c(=O)n1-c1cccc(C(F)(F)F)c1] 4-{5-[3-(2-Dimethylamino-ethyl)-5-methyl-2-oxo-1-(3-trifluoromethyl-phenyl)-2,3-dihydro-1H-imidazol-4-yl]-pyrazol-1-yl}-benzonitrile | ¹H NMR (400 MHz, d6-DMSO): δ 7.97-7.94 (3H, m), 7.78-7.69 (5H, m), 7.60 (1H, d, J = 7.6 Hz), 6.86 (1H, d, J = 1.8 Hz), 3.62-3.54 (1H, m), 3.45-3.42 (1H, m), 2.29-2.22 (1H, m), 2.16-2.10 (1H, m), 1.88 (6H, s), 1.46 (3H, s) | Rt = 3.37 min, m/z = 481.2 [M + H]+ |
| 30 | 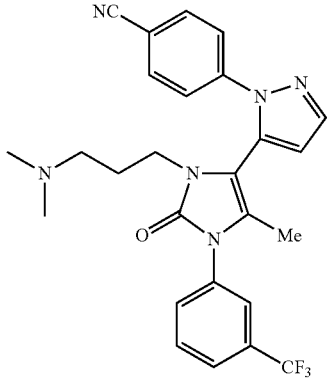 [SMILES: Cc1c(-c2ccnn2-c2ccc(C#N)cc2)n(CCCN(C)C)c(=O)n1-c1cccc(C(F)(F)F)c1] 4-{5-[3-(3-Dimethylamino-propyl)-5-methyl-2-oxo-1-(3-trifluoromethyl-phenyl)-2,3-dihydro-1H-imidazol-4-yl]-pyrazol-1-yl}-benzonitrile | ¹H NMR (400 MHz, d6-DMSO): δ 8.03-7.97 (3H, m), 7.83-7.78 (2H, m), 7.76 (1H, t, J = 8 Hz), 7.72-7.65 (3H, m), 6.87 (1H, d, J = 1.83 Hz), 3.53-3.38 (1H, m), 3.20-3.07 (1H, m), 2.10-2.00 (2H, m), 1.97 (6H, s), 1.68 (3H, s), 1.57-1.42 (1H, m), 1.41-1.26 (1H, m) | Rt = 3.41 min, m/z = 495.3 [M + H]+ |

The following compounds were prepared by analogous procedure to that used in Example 27.

TABLE 4

| Ex | Structure | ¹H NMR | LC-MS Method 3 |
|---|---|---|---|
| 31 | 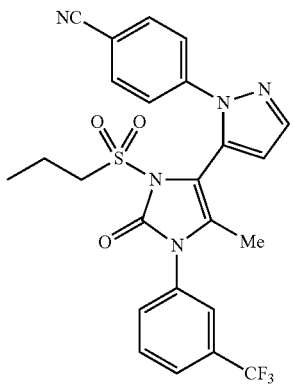 [SMILES: CCCS(=O)(=O)n1c(-c2ccnn2-c2ccc(C#N)cc2)c(C)n(-c2cccc(C(F)(F)F)c2)c1=O] 4-{5-[5[Methyl-2-oxo-3-(propane-1-sulfonyl)-1-(3-trifluoromethyl-phenyl)-2,3-dihydro-1H-imidazol-4-yl]-pyrazol-1-yl}-benzonitrile | ¹H NMR (400 MHz, CDCl₃): δ 7.83 (1H, d, J = 1.7 Hz), 7.78-7.71 (3H, m), 7.69-7.60 (4H, m), 7.55 (1H, dm, J = 7.9 Hz), 6.61 (1H, d, J = 1.8 Hz), 3.51 (1H, ddd, J = 14, 9, and 6 Hz), 3.11 (1H, ddd, J = 14, 9, and 6 Hz), 1.89 (3H, s), 1.71-1.57 (2H, m), 0.96 (3H, t, J = 7.5 Hz) | Rt = 4.98 min, m/z = 516.2 [M + H]+ |

TABLE 4-continued

| Ex | Structure | ¹H NMR | LC-MS Method 3 |
|---|---|---|---|
| 32 | 4-{5-[3-Cyclopropanesulfonyl-5-methyl-2-oxo-1-(3-trifluoromethyl-phenyl)-2,3-dihydro-1H-imidazol-4-yl]-pyrazol-1-yl}-benzonitrile | ¹H NMR (400 MHz, d6-DMSO): δ 8.03-7.95 (3H, m), 7.93-7.84 (3H, m), 7.83 (1H, tm, J = 7.7Hz), 7.75-7.68 (2H, m), 6.78 (1H, d, J = 1.75 Hz), 2.99 (1H, m), 1.87 (3H, s), 1.12-0.93 (3H, m), 0.81-0.73 (1H, m), no NH observed | Rt = 4.87 min, m/z = 514.2 [M + H]+ |
| 33 | 5-[2-(4-Cyano-phenyl)-2H-pyrazol-3-yl]-4-methyl-2-oxo-3-(3-trifluoromethyl-phenyl)-2,3-dihydro-imidazole-1-sulfonic acid ethylamide | ¹H NMR (400 MHz, d6-DMSO): δ 8.51 (1H, t, J = 5.7 Hz), 7.96-7.92 (3H, m), 7.87-7.84 (2H, m), 7.80-7.79 (2H, m), 7.68-7.64 (2H, m), 6.69 (1H, d, J = 1.8 Hz), 2.59-2.42 (2H, m), 1.85 (3H, s), 0.84 (3H, t, J = 7.3 Hz) | Rt = 4.86 min, m/z = 517.2 [M + H]+ |
| 34 | 5-[2-(4-Cyano-phenyl)-2H-pyrazol-3-yl]-4-methyl-2-oxo-3-(3-trifluoromethyl-phenyl)-2,3-dihydro-imidazole-1-sulfonic acid cyclopentylamide | ¹H NMR (400 MHz, d6-DMSO): δ 8.65 (1H, d, J = 7.9 Hz), 8.01-7.95 (2H, m), 7.93 (1H, m), 7.92-7.87 (2H, m), 7.87-7.78 (2H, m), 7.73-7.66 (2H, m), 6.71 (1H, d, J = 1.75 Hz), 2.79 (1H, m) 1.93 (3H, s), 1.60-1.43 (4H, m), 1.42-1.16 (4H, m) | Rt = 5.17 min, m/z = 557.2 [M + H]+ |

TABLE 4-continued

| Ex | Structure | ¹H NMR | LC-MS Method 3 |
|---|---|---|---|
| 35 | 5-[2-(4-Cyano-phenyl)-2H-pyrazol-3-yl]-4-methyl-2-oxo-3-(3-trifluoromethyl-phenyl)-2,3-dihydro-imidazole-1-sulfonic acid cyclopropylamide | ¹H NMR (400 MHz, d6-DMSO): δ 8.95 (1H, bs), 8.00-7.93 (3H, m), 7.92-7.86 (2H, m), 7.85-7.78 (2H, m), 7.75-7.68 (2H, m), 6.71 (1H, d, J = 1.77 Hz), 2.16 (1H, m), 1.84 (3H, s), 0.54-0.37 (3H, m), 0.37-0.28 (1H, m) | Rt = 4.85 min, m/z = 529.1 [M + H]+ |

The following compounds were prepared by analogous procedure to that used in Example 23. In the table below, where rotameric signals have been identified in the NMR spectrum, these have been labelled by *.

TABLE 5

| Ex | Structure | ¹H NMR | LC-MS Method 3 |
|---|---|---|---|
| 36 | 4-{5-[5-Methyl-2-oxo-3-(2-oxo-2-pyrrolidin-1-yl-ethyl)-1-(3-trifluoromethyl-phenyl)-2,3-dihydro-1H-imidazol-4-yl]-pyrazol-1-yl}-benzonitrile | ¹H NMR (400 MHz, d6-DMSO): δ 8.02-7.97 (2H, m), 7.96-7.90 (3H, m), 7.81-7.71 (2H, m), 7.65 (1H, m), 7.55 (1H, dm, J = 7.7 Hz), 6.79 (1H, d, J = 1.8 Hz), 4.44 (2H, s), 3.41-3.35 (2H, m), 3.24-3.09 (2H, m), 1.88-1.79 (2H, m), 1.74-1.65 (2H, m), 1.29 (3H, s) | Rt = 4.43 min, m/z = 521.2 [M + H]+ |
| 37 | 2-[5-[2-(4-Cyano-phenyl)-2H-pyrazol-3-yl]-4-methyl-2-oxo-3-(3-trifluoromethyl-phenyl)-2,3-dihydro-imidazol-1-yl]-N,N-dimethyl-acetamide | ¹H NMR (400 MHz, d6-DMSO): δ 8.01-7.99 (2H, m), 7.94-7.91 (3H, m), 7.81-7.71 (2H, m), 7.65 (1H, m), 7.58 (1H, dm, J = 7.8 Hz), 6.79 (1H, d, J = 1.9 Hz), 4.92-4.51 (2H, m), 2.97 (3H, s), 2.76 (3H, s), 1.31 (3H, s) | Rt = 4.27 min, m/z = 495.2 [M + H]+ |

TABLE 5-continued

| Ex | Structure | ¹H NMR | LC-MS Method 3 |
|---|---|---|---|
| 38 | 4-{5-[5-Methyl-3-[2-(4-methyl-piperazin-1-yl)-2-oxo-ethyl]-2-oxo-1-(3-trifluoromethyl-phenyl)-2,3-dihydro-1H-imidazol-4-yl]-pyrazol-1-yl}-benzonitrile | ¹H NMR (400 MHz, d6-DMSO): δ 8.03-7.97 (2H, m), 7.95 (1H, d, J = 1.8 Hz), 7.92-7.88 (2H, m), 7.81-7.72 (2H, m), 7.66 (1H, m), 7.58 (1H, d, J = 7.7 Hz), 6.78 (1H, d, J = 1.8 Hz), 4.66-4.52 (2H, m), 3.46-3.39 (2H, m), 3.39-3.32 (2H, m), 2.23-2.23 (2H, m), 2.23-2.07 (2H, m), 2.16 (3H, s), 1.32 (3H, s) | Rt =3.33 min, m/z =550.2 [M + H]+ |
| 39 | 2-[5-[2-(4-Cyano-phenyl)-2H-pyrazol-3-yl]-4-methyl-2-oxo-3-(3-trifluoromethyl-phenyl)-2,3-dihydro-imidazol-1-yl]-N-(3-dimethylamino-propyl)-acetamide formic acid salt | ¹H NMR (400 MHz, d6-DMSO): δ 8.15 (1H, s), 8.08 (1H, t, J = 5.5 Hz), 7.99-7.93 (2H, m), 7.90 (1H, d, J = 1.8 Hz), 7.88-7.82 (2H, m), 7.78-7.68 (2H, m), 7.64 (1H, m), 7.56 (1H, dm, J = 7.8 Hz), 6.75 (1H, d, J = 1.8 Hz), 4.26-4.10 (2H, m), 3.01-2.91 (2H, m), 2.19-2.12 (2H, m), 2.09 (6H, s), 1.45-1.36 (2H, m), 1.32 (314, s), salt NH not observed | Rt = 3.24 min, m/z = 552.3 [M + H]+ |
| 40 | 2-[5-[2-(4-Cyano-phenyl)-2H-pyrazol-3-yl]-4-methyl-2-oxo-3-(3-trifluoromethyl-phenyl)-2,3-dihydro-imidazol-1-yl]-N-cyclobutyl-N-methyl-acetamide | ¹H NMR (400 MHz, d6-DMSO): δ 8.03-7.97 (2H, m), 7.94-7.87 (3H, m), 7.78 (1H, dm, J = 7.8 Hz), 7.74 (1H, tm, J = 7.8), 7.65 (1H, bs), 7.58 (1H, dm, J = 7.7), 6.78 (0.5H*, d, J = 1.5 Hz), 6.76 (0.5H*, d, J = 1.5 Hz), 4.71-4.27 (3H, m), 2.91 (1.5H*, s), 2.74 (1.5H*, s), 2.27-1.79 (4H, m), 1.69-1.49 (214, m), 1.33 and 1.31 (3H*, 2 singlets) | Rt = 4.80 min, m/z = 535.4 [M + H]+ |

The following compounds were prepared by analogous procedure to that used in Example 6. Where salts of amines were used in place of the free base, additional triethylamine was added to the reaction mixture to allow for this. In the table below, where rotameric signals have been identified in the NMR spectrum, these have been labelled by *.

TABLE 6

| Ex | Structure | ¹H NMR | LC-MS Method 3 |
|---|---|---|---|
| 41 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid cyclobutylamide | ¹H NMR (400 MHz, d6-DMSO): δ 8.37 (1H, d, J = 7.6 Hz), 7.97 (1H, s), 7.89-7.76 (6H, m), 7.62-7.59 (2H, m), 6.60 (1H, d, J = 1.8 Hz), 3.83 (1H, sext. J = 7.8 Hz), 2.06-1.90 (2H, m), 1.84 (3H, s), 1.81-1.73 (1H, m), 1.68-1.46 (3H, m) | Rt = 5.24 min, m/z = 507.2 [M + H]+ |
| 42 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid cyclopropylamide | ¹H NMR (400 MHz, d6-DMSO): δ 8.32 (1H, d, J - 3.1 Hz), 7.98 (1H, bs), 7.94-7.87 (3H, m), 7.86 (1H, d, J = 1.75 Hz), 7.85-7.78 (2H, m), 7.86 (1H, d, J = 1.75 Hz), 7.85-7.78 (2H, m), 7.69-7.64 (2H, m), 6.34 (1H, d, J = 1.75 Hz), 2.38 (1H, octet), 0.63-0.49 (2H, m), 0.39-0.28 (1H, m), 0.16-0.05 (1H, m) | Rt = 4.95 min, m/z = 493.2 [M + H]+ |
| 43 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid (1-ethanesulfonyl-piperidin-4-yl)-amide | ¹H NMR (400 MHz, d6-DMSO): δ d 8.50 (0.5H*, d, J = 7.18 Hz), 8.41 (0.5H*, d, J = 7.6 Hz), 8.03 (1H, m), 7.95-7.79 (6H, m), 7.69-7.61 (2H, m), 6.64 (1H, d, J = 1.75 Hz), 3.56-3.39 (1H, m), 3.27-2.83 (6H, m), 1.91 and 1.90 (3H*, 2 x s), 1.69-1.33 (4H, m), 1.23 (1.5H*, t, J = 7.3 Hz), 1.15 (1.5H*, t, J = 7.3 | Rt = 4.93 min, m/z = 628.3 [M + H]+ |

TABLE 6-continued

| Ex | Structure | ¹H NMR | LC-MS Method 3 |
|---|---|---|---|
| 44 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid (tetrahydro-pyran-4-yl)-amide | ¹H NMR (400 MHz, d6-DMSO): δ 8.30 (1H, d, J = 7.2 Hz), 8.02 (1H, m), 7.94-7.90 (2H, m), 7.90-7.87 (1H, m), 7.87-7.82 (3H,m ), 7.68-7.62 (2H, m), 6.64 (1H, bs), 3.74-3.59 (2H, m), 3.52-3.40 (1H, m), 3.32-3.22 (2H, m), 1.90 (3H, s), 1.68-1.57 (1H, m), 1.43-1.26 (2H, m), 1.20-1.03 (1H, m) | Rt = 5.83 min, m/z = 537.2 [M + H]+ 559.2 (M + Na)+ |
| 45 | 5-[2-(4-Cyno-henyl)-2H-pyrazol-3-yl]-4-methyl-2-oxo-3-(3-trifluoromethyl-phenyl)-2,3-dihydro-imidazole-1-carboxylic acid cyclopentylamide | ¹H NMR (400 MHz, d6-DMSO): δ 8.23 (1H, d, J = 6.7 Hz), 8.02 (1H, m) 7.94-7.89 (2H, m), 7.89-7.78 (4H, m), 7.67-7.62 (2H, m), 6.64 (1H, bs), 3.67 (1H, m), 1.90 (3H, s), 1.78-1.63 (1H, m), 1.60-1.38 (5H, , m), 1.35-1.19 (1H, m), 1.08-0.94 (1H, m) | Rt = 5.42 min, m/z = 521.2 [M + H]+ 543.2 (M + Na)+ |
| 46 | 5-[2-(4-Cyano-pheny1)-2H-pyrazol-3-yl]-4-methyl-2-oxo-3-(3-trifluoromethyl-phenyl)-2,3-dihydro-imidazole-1-carboxylic acid ((R)-1-methyl-pyrrolidin-3-yl)-amide | ¹H NMR (400 MHz, d6-DMSO): δ 8.41 (1H*, 2 x d, J = 7 Hz), 8.02 (1H, m), 7.97-7.78 (6H,m), 7.68-7.61 (2H, m), 6.64 (1H*, 2 x s), 3.83 (1H, m), 2.62-2.49 (1H, m), 2.42-1.99 (4H, m), 2.18 (3H, s), 1.98-1.79 (4H, m) | Rt = 3.49 min, m/z = 536.2 [M + H]+ |

TABLE 6-continued

| Ex | Structure | ¹H NMR | LC-MS Method 3 |
|---|---|---|---|
| 47 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid ((S)-1-methyl-pyrrolidin-3-yl)-amide | ¹H NMR (400 MHz, d6-DMSO): δ 8.41 (1H*, 2 x d, J = 7.2 Hz), 8.02 (1H, m), 7.96-7.78 (6H,m), 7.68-7.62 (2H, m), 6.64 (1H*, 2 x s), 3.83 (1H, bs), 2.62-2.49 (1H, m), 2.41-2.00 (4H, m), 2.18 (3H, s), 1.96-1.80 (4H, m) | Rt = 3.49 min, m/z = 536.2 [M + H]+ |
| 48 | Mixture of 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid ((3R,4S)-4-hydroxy-tetrahydro-furan-3-yl)-amide and 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid ((3S,4R)-4-hydroxy-tetrahydro-furan-3-yl)-amide | ¹H NMR (400 MHz, d6-DMSO): δ 8.45-8.32 (1H, m), 8.01 (1H, m), 7.97-7.72 (6H, m), 7.71-7.62 (2H, m), 6.65 (1H, d, J = 1.76), 5.30 (1H, m), 3.94 (1H, bs), 3.62-3.38 (5H, m), 1.89 (3H, bs), signals broadened due to presence of rotamers | Rt = 4.38 min, m/z = 539.2 [M + H]+ |
| 49 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid (pyridin-2-ylmethyl)-amide | ¹H NMR (400 MHz, d6-DMSO): δ 9.06 (1H, t, J = 6 Hz), 8.45 (1H, ddd, J+324.9, 1.7 and 1 Hz), 8.04 (1H, m), 7.94-7.80 (6H, m), 7.69 (1H, td, J = 7.8 and 1.8 Hz), 7.67-7.62 (2H, m), 7.26 (1H, ddd, J+327.8, 4.9, and 1 Hz), 6.98 (1H, dm, J = 7.8 Hz), 6.64 (1H, d, J = 1.76 Hz), 4.27 (2H, m), 1.89 (3H, s) | Rt = 4.30 min, m/z = 544.2 [M + H]+ |

TABLE 6-continued

| Ex | Structure | ¹H NMR | LC-MS Method 3 |
|---|---|---|---|
| 50 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid (pyridin-3-ylmethyl)-amide | ¹H NMR (400 MHz, d6-DMSO): δ d 8.89 (1H, t, J = 6 Hz), 8.44 (1H, dd, J = 4.9, 1.7 Hz), 8.28 (1H, dm, J = 1.9 Hz), 8.03 (1H, m), 7.92-7.79 (6H, m), 7.65-7.59 (2H, m), 7.33 (1H, dt, J = 8 and 1.9 Hz), 7.27 (1H, ddd, J = 8, 4.7, and 0.8 Hz), 6.63 (1H, d, J = 1.76 Hz), 4.30-4.06 (2H, m), 1.90 (3H, s) | Rt = 3.84 min, m/z = 544.2 [M + H]+ |
| 51 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid (pyridin-4-ylmethyl)-amide | ¹H NMR (400 MHz, d6-DMSO): δ 8.91 (1H, t, J = 6 Hz), 8.45-8.40 (2H,m), 8.05 (1H, bs), 7.93-7.87 (4H, m), 7.86-7.80 (2H, m), 7.68-7.61 (2H, m), 6.96-6.90 (2H, m), 6.64 (1H, d, J = 1.76 Hz), 4.30-4.09 (2H, m), 1.92 (3H, s) | Rt = 3.69 min, m/z = 544.2 [M + H]+ |
| 52 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid (pyrazin-2-ylmethyl)-amide | ¹H NMR (400 MHz, d6-DMSO): δ 9.07 (1H, t, J = 5.7 Hz), 8.52 (2H, m), 8.30 (1H, m), 8.04 (1H, m), 7.93-7.80 (6H, m), 7.65-7.60 (2H, m), 6.63 (1H, d, J = 1.76 Hz), 4.42-4.26 (2H, m), 1.89 (3H, s) | Rt = 4.57 min, m/z = 545.0 [M + H]+ |

TABLE 6-continued

| Ex | Structure | ¹H NMR | LC-MS Method 3 |
|---|---|---|---|
| 53 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid ((1R,2R)-2-hydroxy-cyclopentyl)-amide | ¹H NMR (400 MHz, d6-DMSO): δ 8.23 (1H, d, J = 6.5 Hz), 8.01 (1H, m), 7.94-7.78 (6H, m), 7.69-7.61 (2H, m), 6.64 (1H, d, J = 1.76 Hz), 4.80-4.63 (1H*, m), 3.75-3.64 (1H, m), 3.47-3.38 (1H*, m), 1.89 (3H, s), 1.77-1.31 (4H, m), 1.30-1.17 (1H, m), 1.04-0.90 (1H, m) | Rt = 4.68 min, m/z = 537.1 [M + H]+ |
| 54 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid (1-methyl-piperidin-4-ylmethyl)-amide | ¹H NMR (400 MHz, d6-DMSO): δ 8.40 (1H, t, J = 6 Hz), 8.03 (1H, m), 7.93-7.79 (6H, m), 7.68-7.61 (1H, m), 6.62 (1H, d, J = 1.74 Hz), 2.97-2.87 (1H, m), 2.79-2.70 (1H, m), 2.69-2.62 (2H, m), 2.11 (3H, s), 1.92 (3H, s), 1.76-1.62 (2H, m), 1.34-1.16 (2H, m), 1.16-1.02 (1H, m), 0.98-0.82 (2H, m) | Rt = 3.56 min, m/z = 564.1 [M + H]+ |

Example 55

3-Methanesulfonyl-4-{5-[5-methyl-2-oxo-1-(3-trifluoromethyl-phenyl)-2,3-dihydro-1H-imidazol-4-yl]-pyrazol-1-yl}-benzonitrile

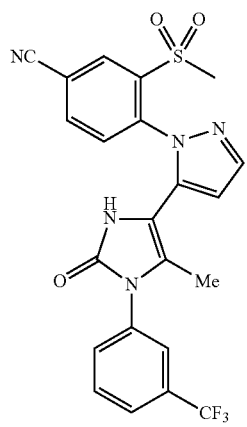 [SMILES: Cc1c(-c2ccnn2-c2ccc(C#N)cc2S(C)(=O)=O)[nH]c(=O)n1-c1cccc(C(F)(F)F)c1]

Intermediate 6

4-{5-[2-Ethoxy-5-methyl-1-(3-trifluoromethyl-phenyl)-1H-imidazol-4-yl]-pyrazol-1-yl}-3-methanesulfonyl-benzonitrile

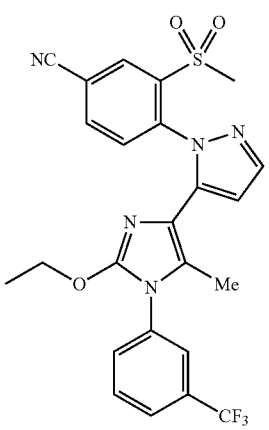 [SMILES: CCOc1nc(-c2ccnn2-c2ccc(C#N)cc2S(C)(=O)=O)c(C)n1-c1cccc(C(F)(F)F)c1]

In a vial were mixed 2-dicyclohexylphosphino-2',4',6'-triisopropylbiphenyl (19 mg, 0.04 mmol) and (2-dicyclohexylphosphino-2',4',6'-triisopropyl-1,1'-biphenyl)palladium(II) dichloride (16 mg, 0.02 mmol), tetrahydroxydiboron (270 mg, 3 mmol) and potassium acetate (294 mg, 3 mmol) and the vial flushed with $N_2$. A solution of 4-bromo-2-ethoxy-5-methyl-1-[3-(trifluoromethyl)phenyl]-1H-imidazole (Intermediate 4, 349 mg, 1 mmol) in IMS (10 ml) was added and the sealed vial heated at 80° C. for 1 h. A degassed solution of $K_2CO_3$ (1.8M, 1.66 ml) was then added followed by a solution of 4-(5-bromo-pyrazol-1-yl)-3-methanesulfonyl-benzonitrile (see DE 102010030187, which is incorporated herein by reference in its entirety, Example 6A, 326 mg, 1 mmol) in THF (3 ml). Heating was continued for a further 2 h. The solution was decanted from the insoluble inorganics and evaporated. The residue was triturated with EtOAc and evaporated again to give an orange gum which was purified by silica chromatography eluting with a gradient of 20% to 100% EtOAc in cyclohexane. Product fractions were combined, evaporated, re-dissolved in MeCN-water and freeze dried to give Intermediate 6 as a white solid (40 mg).

LCMS (Method 2 Rt=3.39 min., m/z 516.3 [M+H]+

3-Methanesulfonyl-4-{5-[5-methyl-2-oxo-1-(3-trifluoromethyl-phenyl)-2,3-dihydro-1H-imidazol-4-yl]-pyrazol-1-yl}-benzonitrile Example 55

The Intermediate 6 was heated in a mixture of acetone (5 ml) and 1M HCl (2 ml) at 60° C. overnight. After cooling, the acetone and most of the water were removed by evaporation in vacuo and the concentrate was diluted with MeCN and water and freeze dried. The crude product (36 mg) was purified by reverse phase chromatography (125 g C18, eluant 10% to 90% MeCN-water containing 0.1% formic acid) to afford the title compound (16 mg).

LCMS (Method 3): Rt=4.18 min, m/z 488.1 [M+H]
$^1$H NMR (400 MHz, d6-DMSO): δ 10.65 (1H, s), 8.52 (1H, d, J=1.8 Hz), 8.35 (1H, dd, J=8.3, 2.0 Hz), 7.93 (1H, d, J=2.0 Hz), 7.76-7.64 (3H, m), 7.65 (1H, d, J=8.3 Hz), 7.56-7.51 (1H, dm, J=7.8 Hz), 6.73 (1H, d, J=1.8 Hz), 3.59 (3H, s), 1.51 (3H, s).

Example 56

5-[2-(2-Bromo-4-cyano-phenyl)-2H-pyrazol-3-yl]-4-methyl-2-oxo-3-(3-trifluoromethyl-phenyl)-2,3-dihydro-imidazole-1-carboxylic acid cyclopentylamide

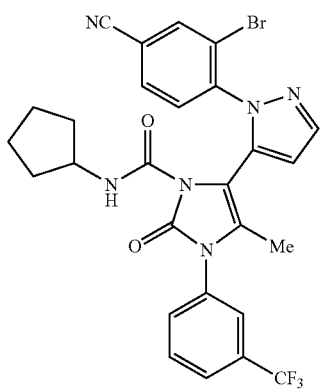 [SMILES: Cc1c(-c2ccnn2-c2ccc(C#N)cc2Br)n(C(=O)NC2CCCC2)c(=O)n1-c1cccc(C(F)(F)F)c1]

Intermediate 7

5-[2-(2-Bromo-4-cyano-phenyl)-2H-pyrazol-3-yl]-4-methyl-2-oxo-3-(3-trifluoromethyl-phenyl)-2,3-dihydro-imidazole-1-carboxylic acid cyclopentylamide

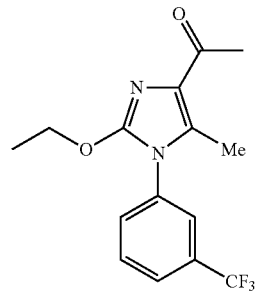 [SMILES: CCOc1nc(C(C)=O)c(C)n1-c1cccc(C(F)(F)F)c1]

1-[2-Ethoxy-5-methyl-1-(3-trifluoromethyl-phenyl)-1H-imidazol-4-yl]-ethanone 4-Bromo-2-ethoxy-5-methyl-1-[3-(trifluoromethyl)phenyl]-1H-imidazole (Intermediate 4, 700 mg, 2 mmol), tributyl(1-ethoxyvinyl)tin (940 mg, 2.6 mmol), bis(triphenyl-phosphine)palladium(II) dichloride (70 mg, 0.1 mmol), DMF (7 ml) and 1M HCl (14 ml) were mixed in each of 3 sealed, degassed ($N_2$) vials which were heated at 120° C. for 1.5 h. The reaction mixtures were combined and treated with 1M HCl (50 ml) and stirred vigorously for 30 min. Water and EtOAc were added and the separated organic phase was washed with water (×2) brine, dried ($Na_2SO_4$) filtered and evaporated to give a brown oil which was purified by chromatography using 10% to 40% EtOAc in cyclohexane to give Intermediate 7 as a yellow oil which crystallised upon cooling (0.91 g, 34%).

LCMS (Method 2) Rt=3.20 min., m/z 285.2 [M+H]+

Intermediate 8

3-Dimethylamino-1-[2-ethoxy-5-methyl-1-(3-trifluoromethyl-phenyl)-1H-imidazol-4-yl]-propenone

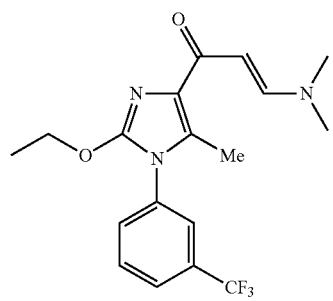 [SMILES: CCOc1nc(C(=O)/C=C/N(C)C)c(C)n1-c1cccc(C(F)(F)F)c1]

1-[2-Ethoxy-5-methyl-1-(3-trifluoromethyl-phenyl)-1H-imidazol-4-yl]-ethanone (Intermediate 7, 1.68 g, 5.38 mmol) and Bredereck's reagent (8 ml) were mixed and heated at 100° C. for a total of 3 h then allowed to stand for 2 days. The Bredereck's reagent was partially evaporated in vacuo at 50° C. and the concentrate was diluted with EtOAc, washed with water (×3), brine, dried ($Na_2SO_4$) and evaporated to give Intermediate 8 as an orange gum which crystallised on standing (1.8 g, 91%).

LCMS (Method 2) Rt=2.85 min., m/z 368.3 [M+H]+

Intermediate 9

3-Bromo-4-{5-[5-methyl-2-oxo-1-(3-trifluoromethyl-phenyl)-2,3-dihydro-1H-imidazol-4-yl]-pyrazol-1-yl}-benzonitrile

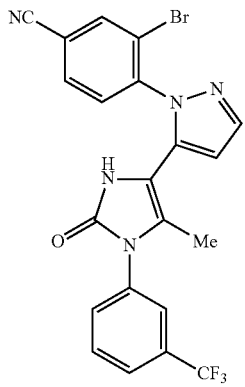 [SMILES: Cc1c(-c2ccnn2-c2ccc(C#N)cc2Br)[nH]c(=O)n1-c1cccc(C(F)(F)F)c1]

3-Dimethylamino-1-[2-ethoxy-5-methyl-1-(3-trifluoromethyl-phenyl)-1H-imidazol-4-yl]-propenone (Intermediate 8, 100 mg, 0.27 mmol) was dissolved in isopropyl alcohol (2 ml) and conc. hydrochloric acid (0.1 ml) was added followed by 3-bromo-4-hydrazino-benzonitrile (70 mg, 0.32 mmol). The solution was heated at 85° C. for 2 h. Solvent was removed in vacuo and the residue was purified by column chromatography using 0% to 100% EtOAc in cyclohexane to give Intermediate 9 as a pink solid (90 mg, 68%).

LCMS (Method U2) Rt=1.39 min., m/z 488.1 and 490.0 [M+H]+(Br isotopes)

5-[2-(2-Bromo-4-cyano-phenyl)-2H-pyrazol-3-yl]-4-methyl-2-oxo-3-(3-trifluoromethyl-phenyl)-2,3-dihydro-imidazole-1-carboxylic acid cyclopentylamide

Example 56

3-Bromo-4-{5-[5-methyl-2-oxo-1-(3-trifluoromethyl-phenyl)-2,3-dihydro-1H-imidazol-4-yl]-pyrazol-1-yl-}-benzonitrile (Intermediate 9, 120 mg, 0.246 mmol), cyclopentyl isocyanate (74 µl, 0.74 mmol) and DIPEA (129 µl, 0.74 mmol) were stirred together in DCM (5 ml) at room temperature for 4 h then at 45° C. overnight. After cooling, the solvent was removed and the product purified by silica gel chromatography eluting with 0% to 50% EtOAc-cyclohexane to afford the title compound as a colourless foam (96 mg, 65%).

LCMS (Method 3): Rt=5.64 min, m/z 599.2 & 601.2 [M+H]+, m/z 621.2 & 623.2 [M+Na]+

$^1$H NMR (400 MHz, CDCl$_3$): δ 8.36-8.32 (1H, d, J=7 Hz), 7.95 (1H, d, J=1.7 Hz), 7.83 (1H, d, J=1.8 Hz), 7.76 (1H, d, J=8.2 Hz), 7.73 (1H, dm, J=7.8 Hz), 7.68 (1H, dd, J=8.2, 1.8 Hz), 7.66 (1H, t, J=7.8 Hz), 7.57-7.55 (1H, m), 7.47 (1H, dm, J=8.2 Hz), 6.55 (1H, d, J=1.7 Hz), 4.00 (1H, tdt, J=6.6, 6.4, 6.7 Hz), 1.93 (3H, s), 1.91-1.89 (2H, m), 1.68-1.56 (4H, m), 1.41-1.30 (2H, m).

Example 57

5-[1-(2-Bromo-4-cyano-phenyl)-1H-pyrazol-3-yl]-4-methyl-2-oxo-3-(3-trifluoromethyl-phenyl)-2,3-dihydro-imidazole-1-carboxylic acid cyclopentylamide

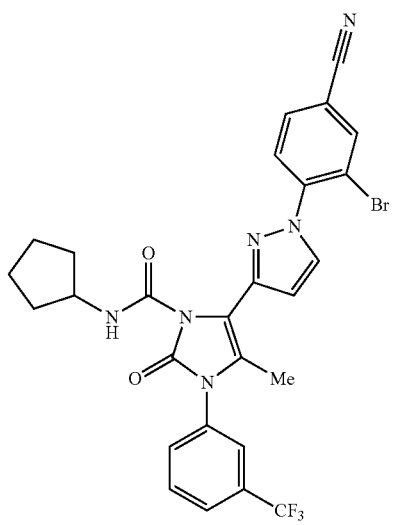 [SMILES: Cc1c(-c2ccn(-c3ccc(C#N)cc3Br)n2)n(C(=O)NC2CCCC2)c(=O)n1-c1cccc(C(F)(F)F)c1]

Intermediate 10

3-Bromo-4-{3-[5-methyl-2-oxo-1-(3-trifluoromethyl-phenyl)-2,3-dihydro-1H-imidazol-4-yl]-pyrazol-1-yl}-benzonitrile 3-Dimethylamino-1-[2-ethoxy-5-methyl-1-(3-trifluoromethyl-phenyl)-1H-imidazol-4-yl]-propenone (Intermediate 8, 540 mg, 1.47 mmol) and 3-bromo-4-hydrazino-benzonitrile (374 mg, 1.76 mmol) were heated together in IPA (15 ml) with conc. hydrochloric acid (5 drops) at 85° C. for 3 h. A further 5 drops of conc. HCl were added and heating was continued for a further 2 h. Solvent was evaporated and the residue was chromatographed (0% to 100% EtOAc-cyclohexane). The first eluting component (31 mg, 4.3%) was Intermediate 10, followed by the 2nd eluting component Intermediate 9 (270 mg, 38%).

LCMS (Method 2) Rt=3.28 min., m/z 488.1 and 490.1 (Br isotopes)

5-[1-(2-Bromo-4-cyano-phenyl)-1H-pyrazol-3-yl]-4-methyl-2-oxo-3-(3-trifluoromethyl-phenyl)-2,3-dihydro-imidazole-1-carboxylic acid cyclopentylamide Example 57

Following the procedure described in Example 56 using cyclopentyl isocyanate Intermediate 10 was converted to the title compound.

LCMS (Method 3): Rt=5.88 min, m/z 599.2 and 601.2 [M+H]+, m/z 621.2 and 623.2 [M+Na]+

$^1$H NMR (400 MHz, d6-DMSO): δ 8.62 (1H, d, J=7.1 Hz), 8.47 (1H, d, J=1.8 Hz), 8.30 (1H, d, J=2.6 Hz), 8.05 (1H, dd, J=8.3, 1.8 Hz), 7.93-7.91 (1H, m), 7.88-7.76 (3H, m), 7.77 (1H, d, J=8.3 Hz), 6.59 (1H, d, J=2.6 Hz), 4.07-3.96 (1H, m), 2.04 (3H, s), 1.91-1.81 (2H, m), 1.67-1.57 (2H, m), 1.56-1.46 (4H, m)

Example 58

5-[2-(4-Cyano-2-fluoro-phenyl)-2H-pyrazol-3-yl]-4-methyl-2-oxo-3-(3-trifluoromethyl-phenyl)-2,3-dihydro-imidazole-1-carboxylic acid cyclopentylamide

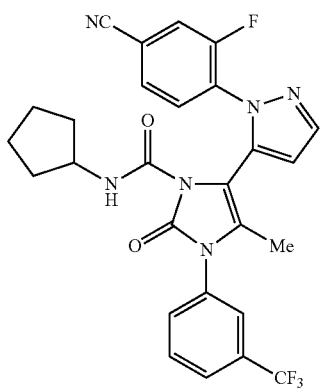 [SMILES: Cc1c(-c2ccnn2-c2ccc(C#N)cc2F)n(C(=O)NC2CCCC2)c(=O)n1-c1cccc(C(F)(F)F)c1]

The title compound was synthesized from 3-fluoro-4-hydrazino-benzonitrile and Intermediate 8 using a similar procedure to that described in Example 56.

LCMS (Method 3): Rt=5.52 min, m/z 539.2 [M+H]+, m/z 561.1 [M+Na]+

$^1$H NMR (400 MHz, CDCl$_3$): δ 8.33 (1H, d, J=6.8 Hz), 7.85 (1H, d, J=1.8 Hz), 7.78-7.72 (2H, m), 7.68 (1H, t, J=7.8 Hz), 7.59 (1H, m), 7.56 (1H, ddd, J=0.9, 1.7, 8.2 Hz), 7.51 (1H, dm, J=8.1 Hz), 7.47 (1H, dd, J=9.7 and 1.7 Hz), 6.57 (1H, d, J=1.8 Hz), 3.90 (1H, ddd, J=12.8, 12.8, 6.9 Hz), 1.94 (3H, s), 1.90-1.75 (2H, m), 1.69-1.50 (4H, m), 1.46-1.32 (1H, m), 1.29-1.16 (1H, m)

Example 59

4-[5'-Methyl-2'-oxo-1'-(3-trifluoromethyl-phenyl)-2',3'-dihydro-1'H-[2,4]biimidazolyl-1-yl]-benzonitrile

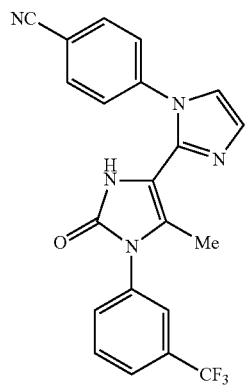 [SMILES: Cc1c(-c2nccn2-c2ccc(C#N)cc2)[nH]c(=O)n1-c1cccc(C(F)(F)F)c1]

Intermediate 11

4-(2-Bromo-imidazol-1-yl)-benzonitrile

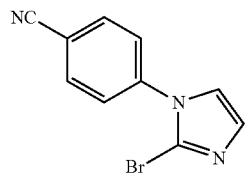 [SMILES: N#Cc1ccc(-n2ccnc2Br)cc1]

4-Imidazol-1-yl-benzonitrile (5.0 g, 29.6 mmol) was dissolved in dioxane and N-bromosuccinimide (5.26 g, 29.6 mmol) was added. The solution was heated at 60° C. for 2 h. The solution was decanted from a gummy residue and evaporated to give a yellow solid. This was triturated with EtOAc to give a cream solid which was further purified by chromatography using EtOAc as eluant to afford Intermediate 11 (0.79 g) as a pale yellow solid.

LCMS (Method 1) Rt=2.44 min., m/z 248 and 250 (Br isotopes)

Intermediate 12

4-[2'-Ethoxy-5'-methyl-1'-(3-trifluoromethyl-phenyl)-1'H-[2,4]biimidazolyl-1-yl]-benzonitrile

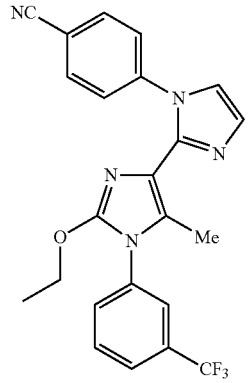

2-Dicyclohexylphosphino-2',4',6'-triisopropylbiphenyl (19 mg, 0.04 mmol), (2-dicyclohexylphosphino-2',4',6'-triisopropyl-1,1'-biphenyl)palladium(II) dichloride (15.7 mg, 0.02 mmol), tetrahydroxydiboron (270 mg, 3 mmol) and potassium acetate (294 mg, 3 mmol) were mixed in a nitrogen filled vial. A solution of 4-bromo-2-ethoxy-5-methyl-1-[3-(trifluoromethyl)phenyl]-1H-imidazole (Intermediate 4, 349 mg, 1 mmol) in IMS (10 ml) was added and the solution heated at 80° C. for 2 h. A solution of K₂CO₃ (1.8M, 1.66 ml) was added followed by a suspension of 4-(2-bromo-imidazol-1-yl)-benzonitrile (Intermediate 11, 248 mg, 1 mmol) in THF. Heating was continued overnight at 80° C. After cooling, the mixture was filtered through celite, washing with EtOAc, and evaporated to dryness. The residue was extracted into EtOAc, decanted, dried over Na₂SO₄ filtered and evaporated. Purification was performed by silica gel chromatography eluting with 20% to 100% EtOAc-cyclohexane. The third eluted component was the title compound (91 mg, 21%).

LCMS (Method 2) Rt=2.73 min., m/z 438.3

4-[5'-Methyl-2'-oxo-1'-(3-trifluoromethyl-phenyl)-2',3'-dihydro-1'H-[2,4]biimidazolyl-1-yl]-benzonitrile Example 59

4-[2'-Ethoxy-5'-methyl-1'-(3-trifluoromethyl-phenyl)-1'H-[2,4]biimidazolyl-1-yl]-benzonitrile (Intermediate 12, 170 mg, 0.39 mmol), acetone (5 ml) and 1M HCl (3 ml) were heated together at 60° C. for 3.5 h. Concentrated HCl (0.5 ml) was added and heating continued overnight. The mixture was cooled and most of the acetone removed by evaporation. The solution was basified with aqueous NaHCO₃ and the white solid title compound filtered off and dried at 50° C. Yield 150 mg (94%).

LCMS (Method 3): Rt=3.61 min, m/z 410.1 [M+H]+

¹H NMR (400 MHz, d6-DMSO): δ 10.47 (1H, s), 8.05-7.99 (2H, m), 7.79-7.73 (3H, m), 7.72 (1H, d, J=1.4 Hz), 7.68-7.63 (1H, m), 7.63-7.58 (2H, m), 7.28 (1H, d, J=1.4 Hz), 1.70 (3H, s)

Example 60

1-(4-Cyano-phenyl)-5'-methyl-2'-oxo-1'-(3-trifluoromethyl-phenyl)-1',2'-dihydro-1H-[2,4]biimidazolyl-3'-carboxylic acid cyclopentylamide

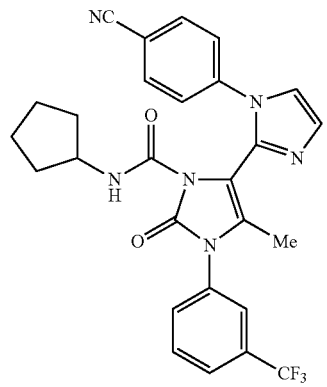 [SMILES: Cc1c(-c2nccn2-c2ccc(C#N)cc2)n(C(=O)NC2CCCC2)c(=O)n1-c1cccc(C(F)(F)F)c1]

4-[5'-Methyl-2'-oxo-1'-(3-trifluoromethyl-phenyl)-2',3'-dihydro-1'H-[2,4]biimidazolyl-1-yl]-benzonitrile (Example 59, 108 mg, 0.26 mmol) was suspended in dry DCM (5 ml) and DIPEA (130 µl, 3 eq.) was added followed by cyclopentyl isocyanate (90 µl, 88 mg, 0.79 mmol). The mixture was heated and stirred at 45° C. for 24 h. The solvent was removed in vacuo and the residue purified by chromatography eluting with EtOAc, thereby yielding the title compound (100 mg, 73%).

LCMS (Method 3): Rt=4.55 min, m/z 521.2 [M+H]+

¹H NMR (400 MHz, d6-DMSO): δ 8.13 (1H, d, J=6.8 Hz), 8.02-7.98 (1H, m), 7.98-7.93 (2H, m), 7.91-7.77 (3H, m), 7.72 (1H, d, J=1.4 Hz), 7.57-7.51 (2H, m), 7.20 (1H, d, J=1.4 Hz), 3.75-3.65 (1H, m), 1.90 (3H, s), 1.75-1.57 (2H, m), 1.56-1.40 (4H, m), 1.35-0.94 (2H, m)

The following compounds were prepared by using an analogous procedure to that in Example 60.

TABLE 7

| Ex | Structure | ¹H NMR | LC-MS Method 3 |
|---|---|---|---|
| 61 | ![structure] 1-(4-Cyano-phenyl)-5'-methyl-2'-oxo-1'-(3-trifluoromethyl-phenyl)-1',2'-dihydro-1H-[2,4']biimidazolyl-3'-carboxylic acid cyclobutylamide | ¹H NMR (400 MHz, CDCl₃): δ 8.51 (1H, d, J = 7.5 Hz), 7.78-7.70 (3H, m), 7.67 (1H, t, J = 7.9 Hz), 7.57-7.55 (1H, m), 7.50-7.42 (3H, m), 7.33 (1H, d, J = 1.3 Hz), 7.27 (1H, d, J = 1.3 Hz), 4.15 (1H, tdt, J = 8.0, 8.0, 8.1 Hz), 2.32-2.19 (2H, m), 1.87 (3H, s), 1.94-1.75 (2H, m), 1.75-1.58 (2H, m) | Rt = 4.37 min, m/z = 507.3 [M + H]+ |

TABLE 7-continued

| Ex | Structure | ¹H NMR | LC-MS Method 3 |
|----|-----------|--------|----------------|
| 62 | ![structure] 1-(4-Cyano-phenyl)-5'-methyl-2'-oxo-1'-(3-trifluoromethyl-phenyl)-1',2'-dihydro-1H-[2,4']biimidazolyl-3'-carboxylic acid 4-methanesulfonyl-benzylamide | ¹H NMR (400 MHz, d6-DMSO): δ 8.84 (1H, t, J = 6 Hz), 8.01 (1H, m), 7.93-7.80 (7H, m), 7.70 (1H, d, J = 1.5 Hz), 7.54-7.51 (2H, m), 7.36-7.29 (2H, m), 7.20 (1H, d, J = 1.5 Hz), 4.28 (2H, d, J = 5.3 Hz), 3.21 (3H, s), 1.89 (3H, s) | Rt = 4.05 min, m/z = 621.3 [M + H]+ |

Example 63

5-[2-(4-Cyano-phenyl)-2H-[1,2,4]triazol-3-yl]-4-methyl-2-oxo-3-(3-trifluoromethyl-phenyl)-2,3-dihydro-imidazole-1-carboxylic acid cyclopentylamide

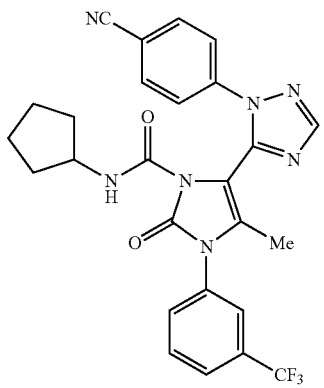 [SMILES: Cc1c(-c2ncnn2-c2ccc(C#N)cc2)n(C(=O)NC2CCCC2)c(=O)n1-c1cccc(C(F)(F)F)c1]

Intermediate 13

4-(5-Bromo-[1,2,4]triazol-1-yl)-benzonitrile

4-[1,2,4]Triazol-1-yl-benzonitrile (1.7 g, 10 mmol) and N-bromosuccinimide (1.78 g, 10 mmol) were heated together in dioxane (50 ml) at 60° C. for 3 h. The mixture was filtered and the filtrate evaporated and the resulting solid was purified by chromatography to give Intermediate 13 as a white solid (0.6 g, 25%).

LCMS (Method 3) Rt=2.61 min., m/z 249 and 251 (Br isotopes)

Intermediate 14

4-{5-[2-Ethoxy-5-methyl-1-(3-trifluoromethyl-phenyl)-1H-imidazol-4-yl]-[1,2,4]triazol-1-yl}-benzonitrile

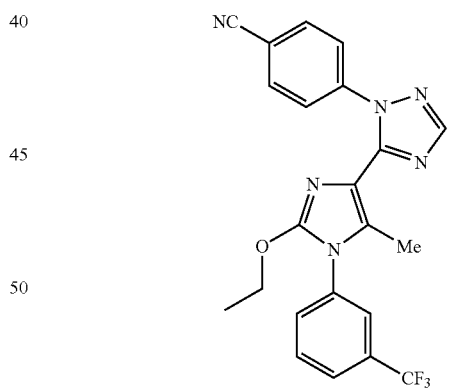

4-Bromo-2-ethoxy-5-methyl-1-[3-(trifluoromethyl)phenyl]-1H-imidazole (Intermediate 4, 349 mg, 1 mmol), 2-dicyclohexylphosphino-2',4',6'-triisopropylbiphenyl (19 mg, 0.04 mmol), (2-dicyclohexylphosphino-2',4',6'-triisopropyl-1,1'-biphenyl)palladium(II) dichloride (15.7 mg, 0.02 mmol), tetrahydroxydiboron (270 mg, 3 mmol), and potassium acetate (294 mg, 3 mmol) and IMS (10 ml) were sealed in each of 2 vials under N₂ and heated at 80° C. for 1.5 h, then 4-(5-bromo-[1,2,4]triazol-1-yl)-benzonitrile (Intermediate 13, 249 mg, 1 mmol) and 1.8M K₂CO₃ (1.66 ml) were added to each vial and heating continued for a further 1 h. The reactions were combined, filtered and evaporated and the residue triturated with DCM to remove more inorganic solids. The solution was chromatographed on silica (0% to 50% EtOAc-DCM) to provide L Intermediate 14 (100 mg, 11.5%).
LCMS (Method U2) Rt=1.55 min., m/z 439.2

Intermediate 15

4-{5-[5-Methyl-2-oxo-1-(3-trifluoromethyl-phenyl)-2,3-dihydro-1H-imidazol-4-yl]-[1,2,4]triazol-1-yl}-benzonitrile

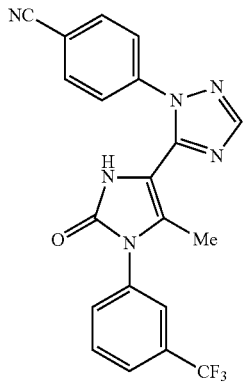

4-{5-[2-Ethoxy-5-methyl-1-(3-trifluoromethyl-phenyl)-1H-imidazol-4-yl]-[1,2,4]triazol-1-yl}-benzonitrile (Intermediate 14, 130 mg, 0.30 mmol), acetone (4 ml) and 5M HCl (3 ml) were heated together at 60° C. for 2 h and allowed to cool. The acetone was removed in vacuo and the aqueous solution basified with NaHCO₃ solution.

The white solid Intermediate 15 was filtered off, washed with water and dried (79 mg, 66%).
LCMS (Method U2) Rt=1.33 min., m/z 411.1

5-[2-(4-Cyano-phenyl)-2H-[1,2,4]triazol-3-yl]-4-methyl-2-oxo-3-(3-trifluoromethyl-phenyl)-2,3-dihydro-imidazole-1-carboxylic acid cyclopentylamide Example 63

4-{5-[5-Methyl-2-oxo-1-(3-trifluoromethyl-phenyl)-2,3-dihydro-1H-imidazol-4-yl]-[1,2,4]triazol-1-yl}-benzonitrile (Intermediate 15, 79 mg, 0.192 mmol), cyclopentyl isocyanate (58 μl, 0.58 mmol) and DIPEA (101 μl, 0.58 mmol) were stirred in DCM (4 ml) at 45° C. overnight. Solvent was evaporated and the product was purified by silica gel chromatography (50% to 100% EtOAc-cyclohexane) to give title compound as a white solid (73 mg, 73%).
LCMS (Method 3): Rt=5.16 min, m/z 522.3 [M+H]+
$^1$H NMR (400 MHz, CDCl₃): δ 8.27 (1H, d, J=6.8 Hz), 8.19 (1H, s), 7.81-7.74 (3H, m), 7.70 (1H, tm, J=8 Hz), 7.67-7.63 (2H, m), 7.61 (1H, m), 7.52 (1H, dm, J=8 Hz), 3.98-3.87 (1H, m), 1.93 (3H, s), 1.91-1.73 (2H, m), 1.69-1.52 (5H, m), 1.47-1.35 (1H, m)

Biological Assay.

Compounds of this invention were tested for potency in a human neutrophil elastase (HNE) enzyme activity assay.

HNE Enzyme Assay.

Assays were performed in 96-well plates in a total assay volume of 100 μL. The final concentration of elastase enzyme (human leukocyte elastase, Sigma E8140) was 0.00072 U/mL. The peptide substrate (MeOSuc-Ala-Ala-Pro-Val-AMC, Calbiochem #324740) was used at a final concentration of 100 μM. The final concentration of DMSO was 1% in the assay buffer (0.05M Tris.HCl, 0.1M NaCl, 0.1M CaCl₂, 0.0005% brij-35, pH 7.5). The enzymatic reaction was started by addition of the enzyme and incubated at 25° C. for 30 minutes. After incubation, the reaction was stopped by addition of soybean trypsin inhibitor (Sigma T9003) at a final concentration of 50 μg/well. Fluorescence was measured using a Molecular Devices fluorescence plate reader using 380 nm excitation and 460 nm emission wavelengths.

A dose response to each compound was performed and the effect of compound in each experiment was expressed as a percentage inhibition of the control enzyme fluorescence. Dose response curves were plotted and compound potency (IC₅₀) was determined. Compounds were tested in at least two separate experiments. IC₅₀ values for tested Examples, representative of the invention, are shown in Table 8:

TABLE 8

| Example | FINE inhibition |
|---------|-----------------|
| 1 | ++ |
| 2 | +++ |
| 3 | +++ |
| 4 | ++++ |
| 5 | +++ |
| 6 | ++++ |
| 7 | +++ |
| 8 | ++++ |
| 9 | +++ |
| 10 | ++++ |
| 11 | ++++ |
| 12 | +++ |
| 13 | ++++ |
| 14 | ++++ |
| 15 | ++++ |
| 16 | ++++ |
| 17 | ++++ |
| 18 | ++++ |
| 19 | ++++ |
| 20 | ++ |
| 21 | ++ |
| 22 | ++ |
| 23 | ++ |
| 24 | +++ |
| 25 | +++ |
| 26 | +++ |
| 27 | ++++ |
| 28 | +++ |
| 29 | +++ |
| 30 | +++ |
| 31 | +++ |
| 32 | ++++ |
| 33 | +++ |
| 34 | ++++ |
| 35 | +++ |
| 36 | +++ |
| 37 | +++ |
| 38 | +++ |
| 39 | ++ |
| 40 | +++ |
| 41 | ++++ |
| 42 | ++++ |
| 43 | ++++ |
| 44 | ++++ |
| 45 | ++++ |
| 46 | ++++ |
| 47 | ++++ |
| 48 | ++++ |
| 49 | +++ |
| 50 | +++ |
| 51 | ++++ |
| 52 | +++ |
| 53 | ++++ |
| 54 | +++ |
| 55 | + |

TABLE 8-continued

| Example | FINE inhibition |
|---------|-----------------|
| 56 | +++ |
| 57 | ++ |
| 58 | ++++ |
| 59 | ++ |
| 60 | ++++ |
| 61 | ++++ |
| 62 | ++++ |
| 63 | ++++ |

In the table above, HNE enzyme inhibition ($IC_{50}$ values) are indicated as follows: >50 nM '+'; 10-50 nM '++'; 1-10 nM '+++'; <1 nM '++++'.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

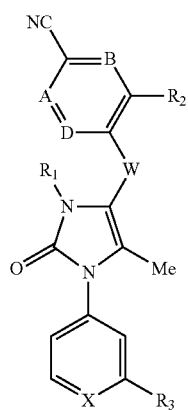

(I)

wherein
A is —CH or —N—;
B is —CH or —N—;
D is —CH or —N—;
X is —CH or —N—;
$R_3$ is —$CF_3$, $CHF_2$, or halogen;
W is a 5 or 6-membered heteroaryl ring, optionally substituted with one or more substituents selected from the group consisting of —CN, —$NO_2$, —O($C_1$-$C_6$)alkyl, —($C_1$-$C_3$)alkyl-O—($C_1$-$C_6$)alkyl, —($C_1$-$C_3$)alkylamino, —($C_3$-$C_8$)cycloalkyl, —OH, ($C_1$-$C_3$)alkyl, halo, —$CF_3$, and —$SO_2$($C_1$-$C_4$)alkyl;
$R_1$ is H, —C(O)$R_4$, —($CH_2$)$_t$—(CHR$_6$)$_n$—$R_4$, —($CH_2$)$_t$—(CHR$_6$)$_n$S($O_2$)—NR$_4$R$_5$, —S($O_2$)—$R_4$, —($CH_2$)$_t$-CHR$_6$)$_n$—C(O)—NR$_4$R$_5$, or —($CH_2$)$_t$—(CHR$_6$)$_n$—C(O)O—$R_4$, $R_4$ is H or is selected from the group consisting of —($C_1$-$C_6$)alkyl, —($C_2$-$C_6$)alkyl-NR$_7$R$_8$, —($C_2$-$C_6$)alkyl-$N^+$R$_7$R$_8$R$_9$, —($C_2$-$C_6$)alkyl-O—($C_1$-$C_4$)alkyl, —($C_2$-$C_6$)alkyl-S($O_2$)($C_1$-$C_4$)alkyl, —($CH_2$)$_t$-aryl, —($CH_2$)$_t$—($C_3$-$C_8$)cycloalkyl, —($CH_2$)$_t$—($C_3$-$C_8$)heterocycloalkyl, and —($CH_2$)$_t$-heteroaryl, optionally substituted with one or more substituents selected from the group consisting of —CN, —$NO_2$, —O($C_1$-$C_6$)alkyl, —($C_1$-$C_3$)alkyl-O—($C_1$-$C_6$)alkyl, —($C_1$-$C_3$)alkylamino, —($C_3$-$C_8$)cycloalkyl, —OH, ($C_1$-$C_3$)alkyl, halo, —$CF_3$, and —$SO_2$($C_1$-$C_4$)alkyl;
n is 0 or an integer of 1, 2 or 3;
t is 0 or an integer of 1, 2 or 3;
$R_5$ is H or —($C_1$-$C_6$)alkyl;
$R_6$ is H, —($C_1$-$C_6$)alkyl, —$CF_3$, or —$CHF_2$;
$R_7$ is H or —($C_1$-$C_6$)alkyl;
$R_8$ is H or —($C_1$-$C_6$)alkyl;
$R_9$ is H or —($C_1$-$C_6$)alkyl;
or, alternatively, $R_4$ and $R_5$, together with the nitrogen atom to which they are linked, form a ($C_3$-$C_8$)heterocycloalkyl or heteroaryl ring system, optionally substituted with one or more substituents selected from the group consisting of —CN, —$NO_2$, —O($C_1$-$C_6$)alkyl, —($C_1$-$C_3$)alkyl-O—($C_1$-$C_6$)alkyl, —($C_1$-$C_3$)alkylamino, —($C_3$-$C_8$)cycloalkyl, —OH, ($C_1$-$C_3$)alkyl, halo, —$CF_3$, and —$SO_2$($C_1$-$C_4$)alkyl, wherein said ($C_3$-$C_8$)heterocycloalkyl or heteroaryl ring system contains a maximum of three hetero-atoms or hetero-groups selected from the group consisting of —N, —NH, —O, —S—, and —$SO_2$; and
$R_2$ is H, —SMe, —S(O)$R_7$, —S($O_2$)$R_7$, or halogen,
or a pharmaceutically acceptable salt thereof.
2. The compound or pharmaceutically acceptable salt according to claim 1, wherein A, B, D and X are —CH.
3. The compound or pharmaceutically acceptable salt according claim 1, wherein W is apyrazolyl, imidazolyl, or tiazolyl ring.
4. The compound or pharmaceutically acceptable salt according to claim 1, wherein $R_3$ is —$CF_3$.
5. The compound or pharmaceutically acceptable salt according to claim 1, wherein $R_2$ is H, halogen, or —S($O_2$)$R_7$ wherein $R_7$ is —($C_1$-$C_6$)alkyl.
6. The compound or pharmaceutically acceptable salt according to claim 1, wherein $R_1$ is —($CH_2$)$_t$—(CHR$_6$)$_n$—C(O)—NR$_4$R$_5$ wherein $R_4$ is H or —($C_1$-$C_6$)alkyl, optionally substituted with one or more groups selected from the group consisting of —O($C_1$-$C_6$)alkyl, —($C_1$-$C_3$)alkylamino, —$SO_2$($C_1$-$C_4$)alkyl, and —OH or $R_4$ is —($CH_2$($C_3$-$C_8$)cycloalkyl, —($CH_2$)$_t$—($C_3$-$C_8$)heterocycloalkyl, —($C_2$-$C_6$)alkyl-NR$_7$R$_8$, —($CH_2$)$_t$-aryl, —($CH_2$)$_t$-heteroaryl, and —($C_2$-$C_6$)alkyl-$N^+$R$_7$R$_8$R$_9$, optionally substituted with one or more of —($C_1$-$C_6$)alkyl or —$SO_2$($C_1$-$C_4$)alkyl; $R_5$ is H or —($C_1$-$C_6$)alkyl; or alternatively $R_4$ and $R_5$, together with the nitrogen atom to which they are linked, form a ($C_3$-$C_8$)heteocycloalkyl or heteroaryl ring system, optionally substituted with one or more substituents selected from the group consisting of —OH and ($C_1$-$C_3$)alkyl, wherein said ($C_3$-$C_8$)heteocycloalkyl or heteroaryl ring system contains a maximum of three hetero-atoms or hetero-groups selected from the group consisting of —N, —NH, —O, —S—, and —$SO_2$; $R_6$ is H, —($C_1$-$C_6$)alkyl, —$CF_3$ or —$CHF_2$; $R_7$ is H or —($C_1$-$C_6$)alkyl; $R_8$ is H or —($C_1$-$C_6$)alkyl; t is 0 or an integer of 1, 2 or 3; and n is 0 or an integer selected from 1, 2 or 3.
7. The compound or pharmaceutically acceptable salt according to claim 1, wherein $R_1$ is —($CH_2$)$_t$—(CHR$_6$)$_n$—C(O)O—$R_4$, $R_4$ is H or —($C_1$-$C_6$)alkyl, optionally substituted with one or more substituents selected from the group consisting of —CN, —NO$_2$, —O(C$_1$-C$_6$)alkyl, —OH, (C$_1$-C$_3$) alkyl, halo, and —CF$_3$; R$_6$ is H, —(C$_1$-C$_6$)alkyl, —CF$_3$ or —CHF$_2$; t is 0 or an integer selected from 1, 2 or 3; and n is 0 or an integer selected from 1, 2 or 3.

8. The compound or pharmaceutically acceptable salt according to claim 1, wherein R$_1$ is —(CH$_2$)$_t$—(CHR$_6$)$_n$S (O$_2$)—NR$_4$R$_5$ wherein R$_4$ is H, —(C$_1$-C$_6$)alkyl, or —(C$_3$-C$_8$) cycloalkyl; R$_5$ is H or —(C$_1$-C$_6$)alkyl; t is 0 or an integer selected from 1, 2 or 3; and n is 0 or an integer selected from 1, 2 or 3.

9. The compound or pharmaceutically acceptable salt according to claim 1, wherein R$_1$ is —S(O$_2$)—R$_4$, R$_4$ is H or —(CH$_2$)$_t$—(C$_3$-C$_8$)cycloalkyl, or —(C$_1$-C$_6$)alkyl; and t is 0 or an integer selected from 1, 2 or 3.

10. The compound or pharmaceutically acceptable salt according to claim 1, which is a compound selected from the group consisting of 4-(5-{5-methyl-2-oxo-1-[3-(trifluoromethyl)phenyl]-2,3-dihydro-1H-imidazol-4-yl}-1H-pyrazol-1-yl)benzonitrile;

4-(5-{5-methyl-3-[3-(methylsulfonyl)propyl]-2-oxo-1-[3-(trifluoromethyl)phenyl]-2,3-dihydro-1H-imidazol-4-yl}-1H-pyrazol-1-yl)benzonitrile;

4-(5-{3,5-dimethyl-2-oxo-1-[3-(trifluoromethyl)phenyl]-2,3-dihydro-1H-imidazol-4-yl}-1H-pyrazol-1-yl)benzonitrile;

ethyl-5-[1-(4-cyanophenyl)-1H-pyrazol-5-yl]-4-methyl-2-oxo-3-[3-(trifluoromethyl)phenyl]-2,3-dihydro-1H-imidazole-1-carboxylate;

4-(5-{3-acetyl-5-methyl-2-oxo-1-[3-(trifluoromethyl)phenyl]-2,3-dihydro-1H-imidazol-4-yl}-1H-pyrazol-1-yl)benzonitrile;

5-[1-(4-cyanophenyl)-1H-pyrazol-5-yl]-N-ethyl-4-methyl-2-oxo-3-[3-(trifluoromethyl)phenyl]-2,3-dihydro-1H-imidazole-1-carboxamide;

5-[1-(4-cyanophenyl)-1H-pyrazol-5-yl]-N-(2-hydroxyethyl)-4-methyl-2-oxo-3-[3-(trifluoromethyl)phenyl]-2,3-dihydro-1H-imidazole-1-carboxamide;

5-[1-(4-cyanophenyl)-1H-pyrazol-5-yl]-N-(3-hydroxypropyl)-4-methyl-2-oxo-3-[3-(trifluoromethyl)phenyl]-2,3-dihydro-1H-imidazole-1-carboxamide;

5-[1-(4-cyanophenyl)-1H-pyrazol-5-yl]-N-[3-(dimethylamino)propyl]-4-methyl-2-oxo-3-[3-(trifluoromethyl)phenyl]-2,3-dihydro-1H-imidazole-1-carboxamide;

4-(5{-3-butanoyl-5-methyl-2-oxo-1-[3-(trifluoromethyl)phenyl]-2,3-dihydro-1H-imidazol-4-yl}-1H-pyrazol-1-yl)benzonitrile;

5-[1-(4-cyanophenyl)-1H-pyrazol-5-yl]-N-(2-methoxyethyl)-4-methyl-2-oxo-3-[3-(trifluoromethyl)phenyl]-2,3-dihydro-1H-imidazole-1-carboxamide;

5-[1-(4-cyanophenyl)-1H-pyrazol-5-yl]-N-[2-(dimethylamino)ethyl]-4-methyl-2-oxo-3-[3-(trifluoromethyl)phenyl]-2,3-dihydro-1H-imidazole-1-carboxamide;

5-[1-(4-cyanophenyl)-1H-pyrazol-5-yl]-4-methyl-N-[2-(methyl sulfonyl)ethyl]-2-oxo-3-[3-(trifluoromethyl)phenyl]-2,3-dihydro-1H-imidazole-1-carboxamide;

5-[1-(4-cyanophenyl)-1H-pyrazol-5-yl]-4-methyl-2-oxo-N-(tetrahydrofuran-3-yl)-3-[3-(trifluoromethyl)phenyl]-2,3-dihydro-1H-imidazole-1-carboxamide;

5-[1-(4-cyanophenyl)-1H-pyrazol-5-yl]-4-methyl-2-oxo-N-[(3S)-tetrahydrfuran-3-yl]-3-[3-(trifluoromethyl)phenyl]-2,3-dihydro-1H-imidazole-1-carboxamide;

5-[1-(4-cyanophenyl)-1H-pyrazol-5-yl]-4-methyl-2-oxo-N-[(3R)-tetrahydrofuran-3yl]-3-[3-(trifluoromethyl)phenyl]-2,3-dihydro-1H-imidazole-1-carboxamide;

5-[1-(4-cyanophenyl)-1H-pyrazol-5-yl]-4-methyl-N-[(1-methyl-1H-pyrazol-3-yl)methyl]-2-oxo-3-[3-(trifluoromethyl)phenyl]-2,3-dihydro-1H-imidazole-1-carboxamide;

methyl-5-[1-(4-cyanophenyl)-1H-pyrazol-5-yl]-4-methyl-2-oxo-3-[3-(trifluoromethyl)phenyl]-2,3-dihydro-1H-imidazole-1-carboxylate;

4-(5-{5-methyl-2-oxo-3-pentanoyl-1-[3-(trifluoromethyl)phenyl]-2,3-dihydro-1H-imidazol-4-yl}-1H-pyrazol-1-yl)benzonitrile;

tert-butyl-{5-[1-(4-cyanophenyl)-1H-pyrazol-5-yl]-4-methyl-2-oxo-3-[3-(trifluoromethyl)phenyl]-2,3-dihydro-1H-imidazol-1-yl}acetate;

5-[1-(4-cyanophenyl)-1H-pyrazol-5-yl]-N-ethyl-N,4-dimethyl-2-oxo-3-[3-(trifluoromethyl)phenyl]-2,3-dihydro-1H-imidazole-1-carboxamide;

{5-[1-(4-cyanophenyl)-1H-pyrazol-5-yl]-4-methyl-2-oxo-3-[3-(trifluoromethyl)phenyl]-2,3-dihydro-1H-imidazol-1-yl}acetic acid;

2-{5-[1-(4-cyanophenyl)-1H-pyrazol-5-yl]-4-methyl-2-oxo-3-[3-(trifluoromethyl)phenyl]-2,3-dihydro-1H-imidazol-1-yl}-N-methylacetamide;

benzenesulfonate 3-[({5-[1-(4-cyanophenyl)-1H-pyrazol-5-yl]-4-methyl-2-oxo-3-[3-(trifluoromethyl)phenyl]-2,3-dihydro-1H-imidazol-1-yl}carbonyl)amino]-N,N,N-trimethylpropan-1-aminium;

benzenesulfonate 2-[({5-[1-(4-cyanophenyl)-1H-pyrazol-5-yl]-4-methyl-2-oxo-3-[3-(trifluoromethyl)phenyl]-2,3-dihydro-1H-imidazol-1-yl}carbonyl)amino]-N,N,N-trimethylethanaminium;

4-(5-{3-butyl-5-methyl-2-oxo-1-[3-(trifluoromethyl)phenyl]-2,3-dihydro-1H-imidazol-4-yl}-1H-pyrazol-1-yl)benzonitrile;

4-(5-{5-methyl-3-(methylsulfonyl)-2-oxo-1-[3-(trifluoromethyl)phenyl]-2,3-dihydro-1H-imidazol-4-yl}-1H-pyrazol-1-yl)benzonitrile;

4-{5-[5-methyl-3-(1-methyl-butyl)-2-oxo-1-(3-trifluoromethyl-phenyl)-2,3-dihydro-1H-imidazol-4-yl]pyrazol-1-yl}-benzonitrile;

4-{5-[3-(2-dimethylamino-ethyl)-5-methyl-2-oxo-1-(3-trifluoromethyl-phenyl)-2,3-dihydro-1H-imidazol-4-yl]-pyrazol-1-yl}-benzonitrile;

4-{5-[3-(3-dimethylamino-propyl)-5-methyl-2-oxo-1-(3-trifluoromethyl-phenyl)-2,3-dihydro-1H-imidazol-4-yl]-pyrazol-1-yl}-benzonitrile;

4-{5-[5-methyl-2-oxo-3-(propane-1-sulfonyl)-1-(3-trifluoromethyl-phenyl)-2,3-dihydro-1H-imidazol-4-yl]-pyrazol-1-yl}-benzonitrile;

4-{5-[3-cyclopropanesulfonyl-5-methyl-2-oxo-1-(3-trifluoromethyl-phenyl)-2,3-dihydro-1H-imidazol-4-yl]-pyrazol-1-yl}-benzonitrile;

5-[2-(4-cyano-phenyl)-2H-pyrazol-3-yl]-4-methyl-2-oxo-3-(3-trifluoromethyl-phenyl)-2,3-dihydro-imidazole-1-sulfonic acid ethylamide;

5-[2-(4-cyano-phenyl)-2H-pyrazol-3-yl]-4-methyl-2-oxo-3-(3-trifluoromethyl-phenyl)-2,3-dihydro-imidazole-1-sulfonic acid cyclopentylamide;

5-[2-(4-cyano-phenyl)-2H-pyrazol-3-yl]-4-methyl-2-oxo-3-(3-trifluoromethyl-phenyl)-2,3-dihydro-imidazole-1-sulfonic acid cyclopropylamide;

4-{5-[5-methyl-2-oxo-3-(2-oxo-2-pyrrolidin-1-yl-ethyl)-1-(3-trifluoromethyl-phenyl)-2,3-dihydro-1H-imidazol-4-yl]-pyrazol-1-yl}-benzonitrile;

2-[5-[2-(4-cyano-phenyl)-2H-pyrazol-3-yl]-4-methyl-2-oxo-3-(3-trifluoromethyl-phenyl)-2,3-dihydro-imidazol-1-yl]-N,N-dimethyl-acetamide;

4-{5-[5-methyl-3-[2-(4-methyl-piperazin-1-yl)-2-oxo-ethyl]-2-oxo-1-(3-trifluoromethyl-phenyl)-2,3-dihydro-1H-imidazol-4-yl]-pyrazol-1-yl}-benzonitrile;

2-[5-[2-(4-cyano-phenyl)-2H-pyrazol-3-yl]-4-methyl-2-oxo-3-(3-trifluoromethyl-phenyl)-2,3-dihydro-imidazol-1-yl]-N-(3-dimethylamino-propyl)-acetamide formic acid salt;

2-[5-[2-(4-cyano-phenyl)-2H-pyrazol-3-yl]-4-methyl-2-oxo-3-(3-trifluoromethyl-phenyl)-2,3-dihydro-imidazol-1-yl]-N-cyclobutyl-N-methyl-acetamide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid cyclobutylamide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid cyclopropylamide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid (1-ethanesulfonyl-piperidin-4-yl)-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid (tetrahydro-pyran-4-yl)-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid cyclopentylamide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid ((R)-1-methyl-pyrrolidin-3-yl)-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid ((S)-1-methyl-pyrrolidin-3-yl)-amide;

a mixture of 5-[2-(4-cyano-phenyl)-2H-pyrazol-3-yl]-4-methyl-2-oxo-3-(3-trifluoromethyl-phenyl)-2,3-dihydro-imidazole-1-carboxylic acid ((3R,4S)-4-hydroxy-tetrahydro-furan-3-yl)-amide and 5-[2-(4-cyano-phenyl)-2H-pyrazol-3-yl]-4-methyl-2-oxo-3-(3-trifluoromethyl-phenyl)-2,3-dihydro-imidazole-1-carboxylic acid ((3S,4R)-4-hydroxy-tetrahydro-furan-3-yl)-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid (pyridin-2-ylmethyl)-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid (pyridin-3-ylmethyl)-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid (pyridin-4-ylmethyl)-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid (pyrazin-2-ylmethyl)-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid ((1R,2R)-2-hydroxy-cyclopentyl)-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid (1-methyl-piperidin-4-ylmethyl)-amide;

3-methanesulfonyl-4-{5-[5-methyl-2-oxo-1-(3-trifluoromethyl-phenyl)-2,3-dihydro-1H-imidazol-4-yl]-pyrazol-1-yl}-benzonitrile;

5-[2-(2-bromo-4-cyano-phenyl)-2H-pyrazol-3-yl]-4-methyl-2-oxo-3-(3-trifluoromethyl-phenyl)-2,3-dihydro-imidazole-1-carboxylic acid cyclopentylamide;

5-[1-(2-bromo-4-cyano-phenyl)-1H-pyrazol-3-yl]-4-methyl-2-oxo-3-(3-trifluoromethyl-phenyl)-2,3-dihydro-imidazole-1-carboxylic acid cyclopentylamide;

5-[2-(4-cyano-2-fluoro-phenyl)-2H-pyrazol-3-yl]-4-methyl-2-oxo-3-(3-trifluoromethyl-phenyl)-2,3-dihydro-imidazole-1-carboxylic acid cyclopentylamide;

4-[5'-methyl-2'-oxo-1'-(3-trifluoromethyl-phenyl)-2',3'-dihydro-1'H-[2,4]biimidazolyl-1-yl]-benzonitrile;

1-(4-cyano-phenyl)-5'-methyl-2'-oxo-1'-(3-trifluoromethyl-phenyl)-1',2'-dihydro-1H-[2,4]biimidazolyl-3'-carboxylic acid cyclopentylamide;

1-(4-cyano-phenyl)-5'-methyl-2'-oxo-1'-(3-trifluoromethyl-phenyl)-1',2'-dihydro-1H-[2,4]biimidazolyl-3'-carboxylic acid cyclobutylamide;

1-(4-cyano-phenyl)-5'-methyl-2'-oxo-1'-(3-trifluoromethyl-phenyl)-1',2'-dihydro-1H-[2,4]biimidazolyl-3'-carboxylic acid 4-methanesulfonyl-benzylamide; and 5-[2-(4-cyano-phenyl)-2H-[1,2,4]triazol-3-yl]-4-methyl-2-oxo-3-(3-trifluoromethyl-phenyl)-2,3-dihydro-imidazole-1-carboxylic acid cyclopentylamide;

or a pharmaceutically acceptable salt of said compound.

11. The pharmaceutical composition, comprising a compound or pharmaceutically acceptable salt according to claim 1 and one or more pharmaceutically acceptable carriers or excipients.

12. The pharmaceutical composition according to claim 11, which is adapted for oral administration or pulmonary administration.

* * * * *